(12) United States Patent
Racenet et al.

(10) Patent No.: US 9,861,368 B2
(45) Date of Patent: Jan. 9, 2018

(54) CIRCULAR STAPLING INSTRUMENT

(71) Applicant: Covidien LP, Mansfield, MA (US)

(72) Inventors: David Racenet, Killingworth, CT (US); Patrick Mozdzierz, Glastonbury, CT (US); Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 309 days.

(21) Appl. No.: 14/694,234

(22) Filed: Apr. 23, 2015

(65) Prior Publication Data

US 2015/0223818 A1   Aug. 13, 2015

Related U.S. Application Data

(62) Division of application No. 13/365,372, filed on Feb. 3, 2012, now Pat. No. 9,038,882.

(51) Int. Cl.
| | |
|---|---|
| *A61B 17/115* | (2006.01) |
| *A61B 17/072* | (2006.01) |
| *A61B 17/00* | (2006.01) |

(52) U.S. Cl.
CPC ........ *A61B 17/1155* (2013.01); *A61B 17/072* (2013.01); *A61B 17/07207* (2013.01); *A61B 2017/0023* (2013.01); *A61B 2017/00398* (2013.01); *A61B 2017/00464* (2013.01); *A61B 2017/00473* (2013.01); *A61B 2017/00477* (2013.01); *A61B 2017/00734* (2013.01); *A61B 2017/07221* (2013.01); *A61B 2017/07285* (2013.01)

(58) Field of Classification Search
CPC .. A61B 17/1155; A61B 17/072; A61B 17/068
USPC ................ 227/176.1, 179.1, 180.1
See application file for complete search history.

(56) References Cited

U.S. PATENT DOCUMENTS

| | | | |
|---|---|---|---|
| 5,205,459 A | 4/1993 | Brinkerhoff et al. | |
| 5,271,543 A * | 12/1993 | Grant ................... | A61B 17/115 227/179.1 |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,312,024 A | 5/1994 | Grant et al. | |

(Continued)

FOREIGN PATENT DOCUMENTS

| | | |
|---|---|---|
| AU | 2012261489 A1 | 8/2013 |
| EP | 2401969 A1 | 1/2012 |

(Continued)

OTHER PUBLICATIONS

Australian Examination Report dated Oct. 13, 2016 in corresponding Australian Application No. 2013200231.

(Continued)

*Primary Examiner* — Nathaniel Chukwurah

(57) ABSTRACT

A circular stapling instrument including a stapling forming assembly that is actuated independently from actuation of the cutting assembly is provided. The instrument includes a handle assembly, an elongate body extending from the handle assembly, a cartridge assembly mounted on a distal end of the elongate body. The cartridge assembly includes a pusher and a knife assembly. The knife assembly is selectively fixed relative to the pusher.

13 Claims, 21 Drawing Sheets

(56) References Cited

U.S. PATENT DOCUMENTS

| | | | |
|---|---|---|---|
| 5,350,104 A | 9/1994 | Main et al. | |
| 5,392,979 A * | 2/1995 | Green | A61B 17/115 227/179.1 |
| 5,433,721 A | 7/1995 | Hooven et al. | |
| 5,439,156 A | 8/1995 | Grant et al. | |
| 5,445,644 A | 8/1995 | Pietrafitta et al. | |
| 5,609,285 A | 3/1997 | Grant et al. | |
| 5,632,433 A * | 5/1997 | Grant | A61B 17/115 227/176.1 |
| 6,050,472 A | 4/2000 | Shibata | |
| 6,083,241 A | 7/2000 | Longo et al. | |
| 6,102,271 A | 8/2000 | Longo et al. | |
| 6,119,913 A | 9/2000 | Adams et al. | |
| 6,126,058 A | 10/2000 | Adams et al. | |
| 6,179,195 B1 | 1/2001 | Adams et al. | |
| 6,241,140 B1 | 6/2001 | Adams et al. | |
| 6,302,311 B1 | 10/2001 | Adams et al. | |
| 6,343,731 B1 | 2/2002 | Adams et al. | |
| 6,443,973 B1 | 9/2002 | Whitman | |
| 6,478,210 B2 | 11/2002 | Adams et al. | |
| 6,517,565 B1 | 2/2003 | Whitman et al. | |
| 6,585,144 B2 | 7/2003 | Adams et al. | |
| 6,601,749 B2 | 8/2003 | Sullivan et al. | |
| 6,629,630 B2 | 10/2003 | Adams | |
| 6,695,198 B2 | 2/2004 | Adams et al. | |
| 6,716,233 B1 | 4/2004 | Whitman | |
| 6,805,273 B2 | 10/2004 | Bilotti et al. | |
| 6,817,508 B1 | 11/2004 | Racenet et al. | |
| 6,820,791 B2 | 11/2004 | Adams | |
| 6,827,246 B2 | 12/2004 | Sullivan et al. | |
| 6,840,423 B2 | 1/2005 | Adams et al. | |
| 6,866,178 B2 | 3/2005 | Adams et al. | |
| 6,874,669 B2 | 4/2005 | Adams et al. | |
| 6,981,941 B2 | 1/2006 | Whitman et al. | |
| 6,988,650 B2 | 1/2006 | Schwemberger et al. | |
| 7,032,798 B2 | 4/2006 | Whitman et al. | |
| 7,134,587 B2 | 11/2006 | Schwemberger et al. | |
| 7,147,140 B2 | 12/2006 | Wukusick et al. | |
| 7,207,472 B2 | 4/2007 | Wukusick et al. | |
| 7,404,508 B2 | 7/2008 | Smith et al. | |
| 7,410,086 B2 | 8/2008 | Ortiz et al. | |
| 7,419,080 B2 | 9/2008 | Smith et al. | |
| 7,546,939 B2 | 6/2009 | Adams et al. | |
| 7,694,864 B2 | 4/2010 | Okada et al. | |
| 7,784,663 B2 | 8/2010 | Shelton, IV | |
| 7,837,080 B2 | 11/2010 | Schwemberger | |
| 7,845,537 B2 | 12/2010 | Shelton, IV et al. | |
| 7,896,215 B2 | 3/2011 | Adams et al. | |
| 7,959,050 B2 | 6/2011 | Smith et al. | |
| 8,028,885 B2 | 10/2011 | Smith et al. | |
| 8,038,016 B2 | 10/2011 | Yuyama et al. | |
| 2003/0130677 A1 | 7/2003 | Whitman et al. | |
| 2004/0111081 A1 | 6/2004 | Whitman et al. | |
| 2005/0187576 A1 | 8/2005 | Whitman et al. | |
| 2009/0112327 A1 | 4/2009 | Lane et al. | |
| 2009/0145947 A1 | 6/2009 | Scirica et al. | |
| 2009/0173767 A1 | 7/2009 | Milliman | |
| 2009/0179063 A1 | 7/2009 | Milliman et al. | |
| 2009/0230170 A1 | 9/2009 | Milliman | |
| 2011/0218562 A1 | 9/2011 | Viola et al. | |

FOREIGN PATENT DOCUMENTS

| | | |
|---|---|---|
| WO | 2004112583 A2 | 12/2004 |
| WO | 2008003371 A1 | 1/2008 |
| WO | 2009/039506 A1 | 3/2009 |

OTHER PUBLICATIONS

European Office Action dated Jan. 25, 2017, issued in EP Application No. 13153611.
European Search Report EP 13 15 3611 dated Apr. 22, 2015.
Australian Office Action dated Oct. 10, 2017 cited in AU Application No. 2017201179.

* cited by examiner

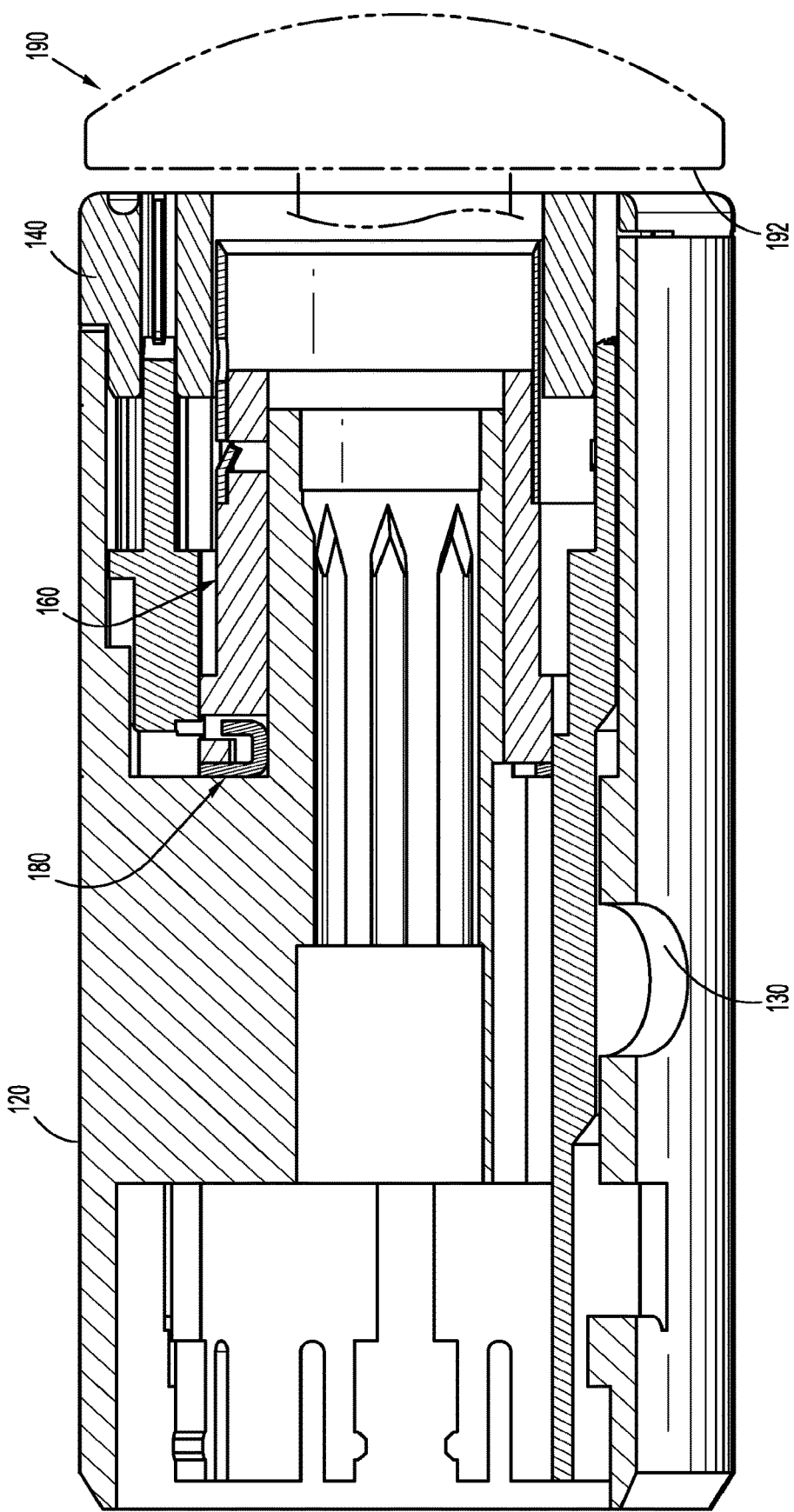

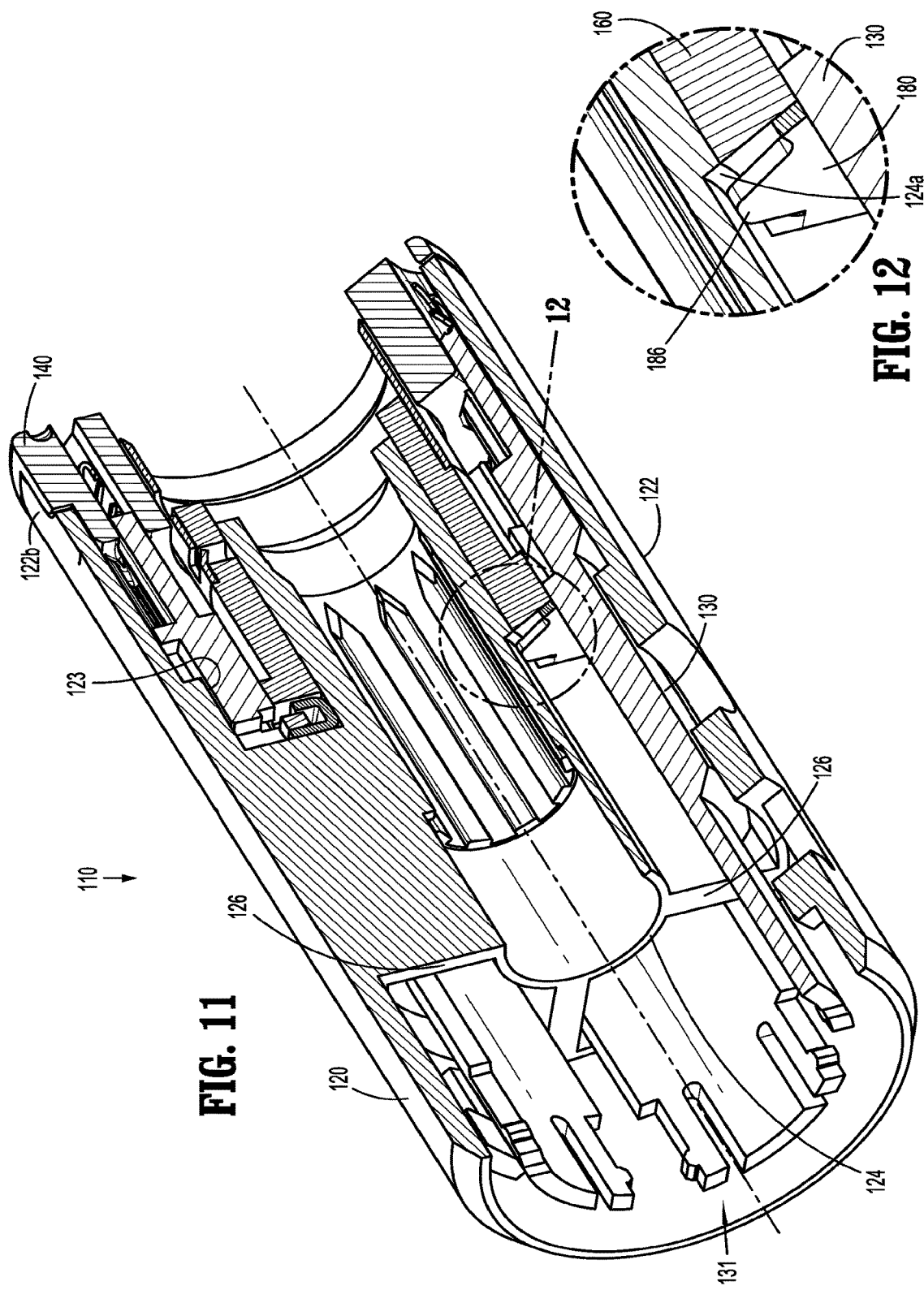

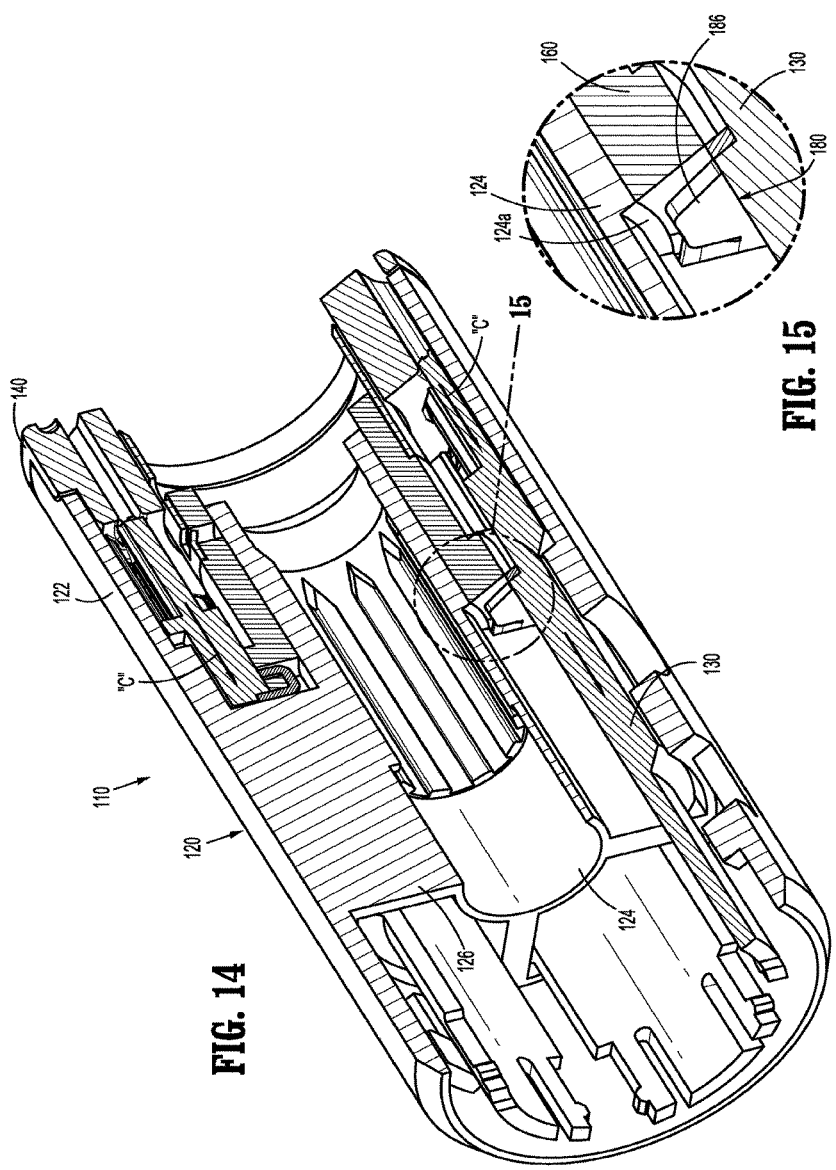

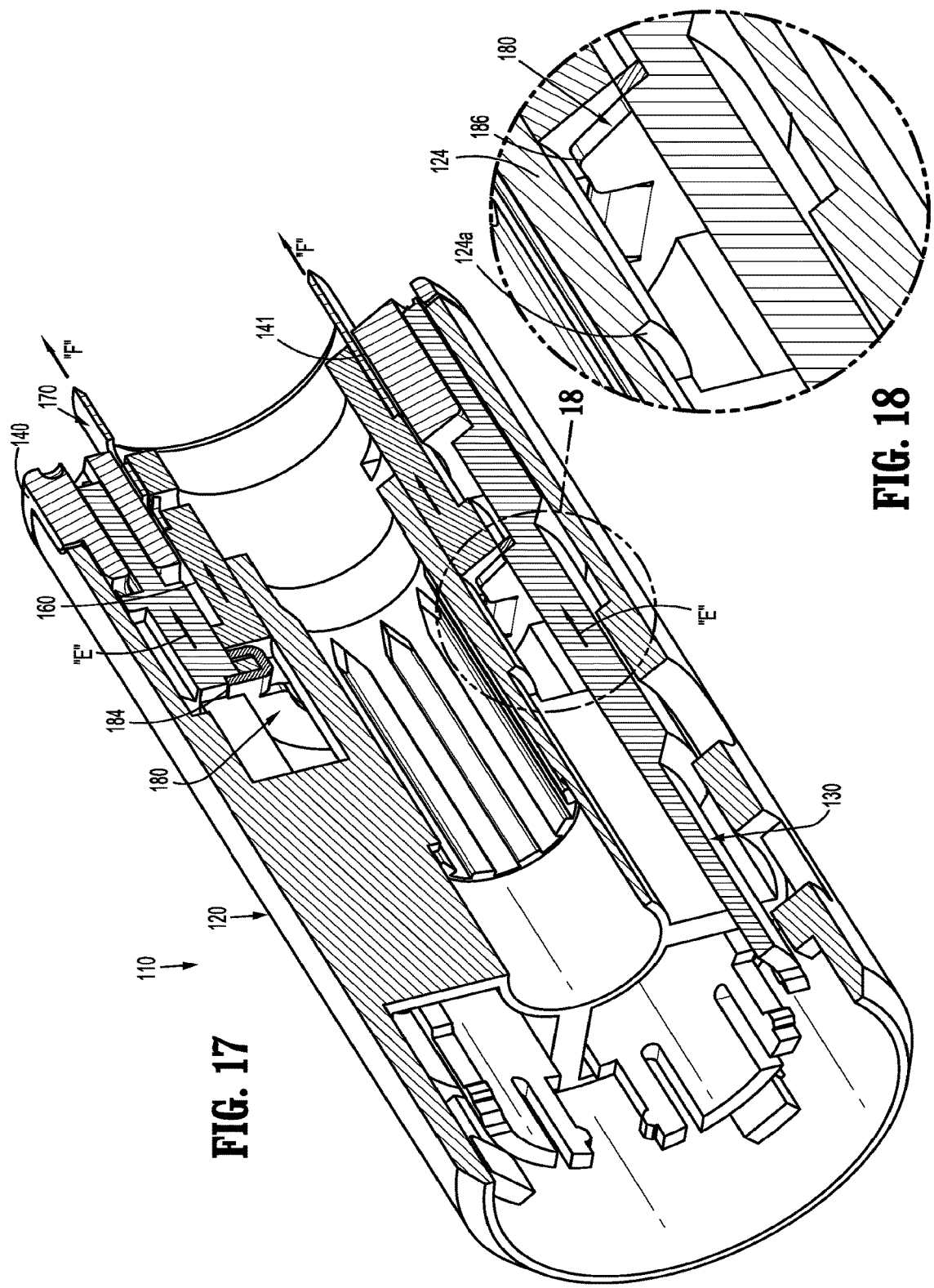

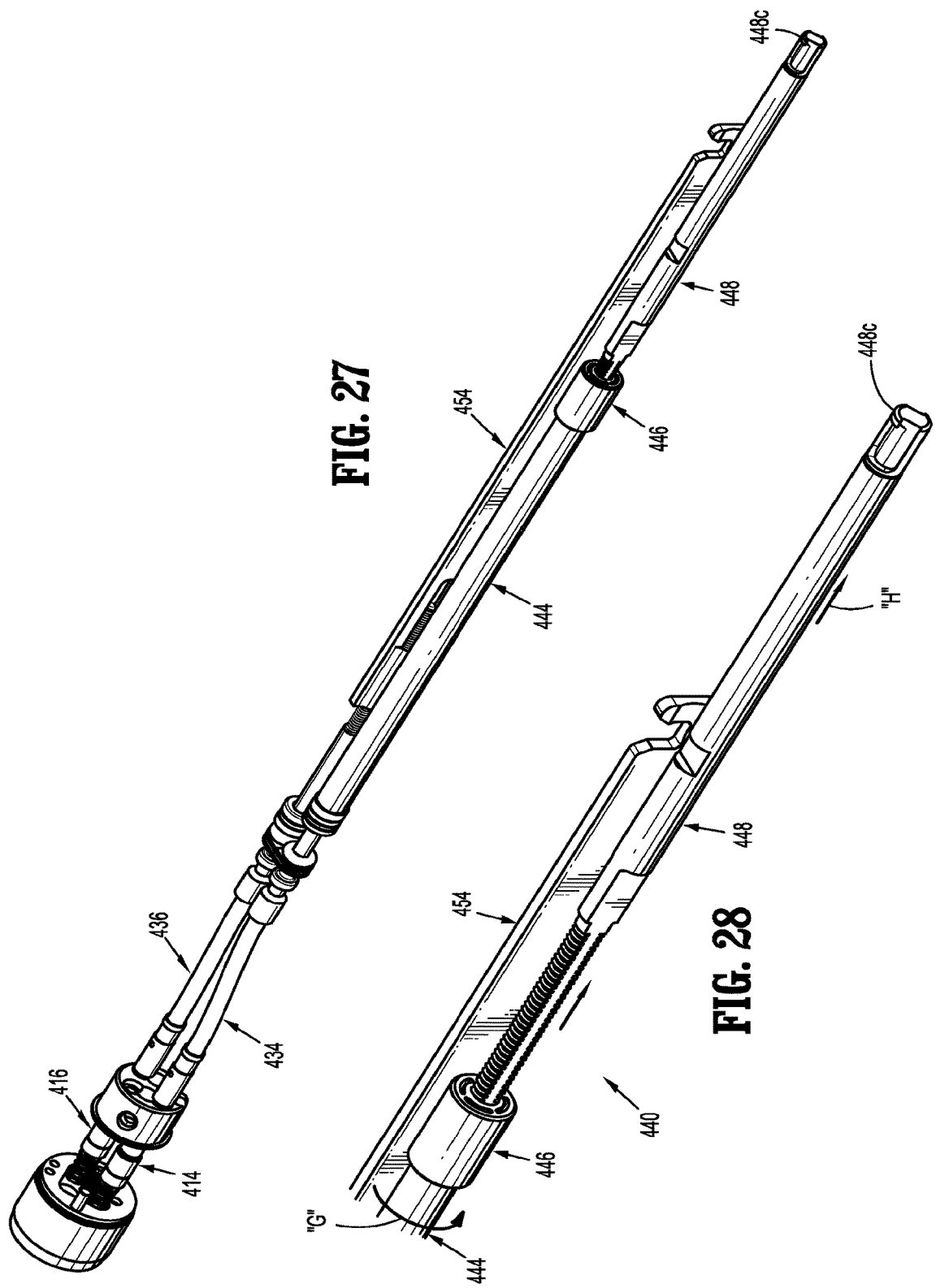

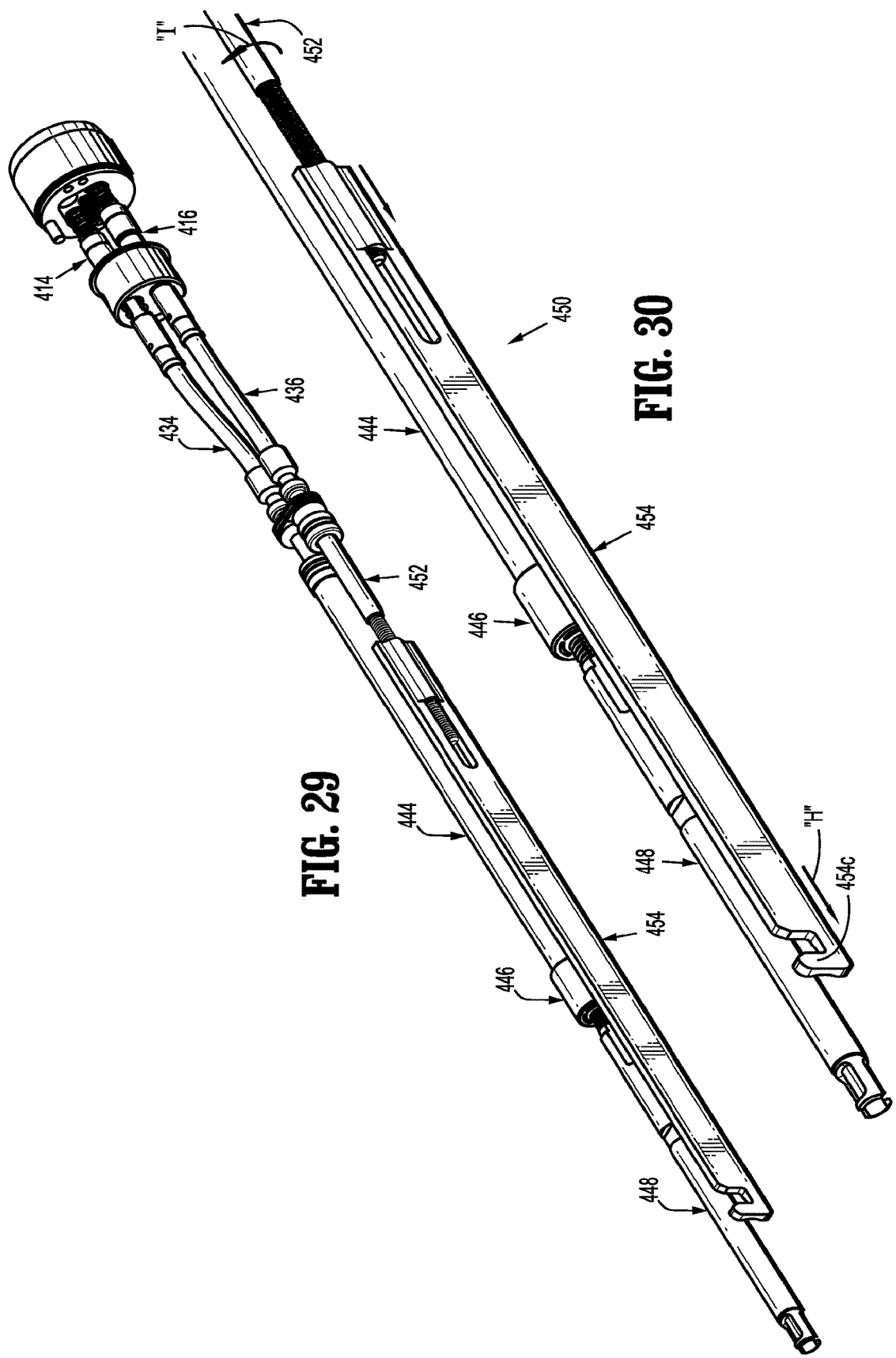

CIRCULAR STAPLING INSTRUMENT

CROSS-REFERENCE TO RELATED APPLICATIONS

This application is a divisional of U.S. patent application Ser. No. 13/365,372 filed Feb. 3, 2012, and the disclosure of the above-identified application is hereby incorporated by reference in its entirety.

BACKGROUND

Technical Field

The present disclosure relates to circular stapling instruments. More particularly, the present disclosure relates to a circular stapling instrument having independent strokes for forming staples and cutting tissue.

Background of Related Art

Circular staplers are known, as are their use in closed procedures, i.e., endoscopic, laparoscopic or through natural body orifices. Typically the circular staplers include a tool assembly on a distal end of an elongate body. The tool assembly includes a mechanism for forming staples and a knife for cutting the stapled tissue. Actuation of the tool assembly may be performed by a manually operated trigger or a powered drive assembly. Generally, both the actuation of the staple forming mechanism and the advancement of the knife occur at the same time, i.e., simultaneously. Thus, the force provided by the actuation assembly must be sufficient to overcome the force required to form the staples and the force required to advance the knife through the tissue being stapled. Further, the simultaneous actuation of the staple forming mechanism and advancement of the knife requires that the staple forming mechanism and the knife travel the same distance, thereby limiting the staple formation height to the knife travel distance.

Therefore, it would be beneficial to have a circular stapler including a tool assembly configured to form staples independently of cutting tissue.

SUMMARY

Accordingly, a circular stapler including a stapling forming assembly that is actuated independently from actuation of the cutting assembly is provided. The circular stapler includes a handle assembly, an elongate body extending from the handle assembly and a cartridge assembly mounted on a distal end of the elongate body. The cartridge assembly includes a pusher and a knife assembly. The knife assembly is selectively fixed relative to the pusher for independent movement relative to the pusher. The pusher may be configured to advance a first distance and retract a second distance, the second distance being greater than the first distance. The pusher may include a groove formed about an inner surface thereof and the knife includes an actuator clip configured to selectively engage the groove. During the first stroke the pusher may be advanced independently of the knife assembly.

In one embodiment, the cartridge assembly may include a housing having an outer cylindrical portion and an inner cylindrical portion. The pusher and knife assembly may be selectively received between the inner and outer cylindrical portions of the housing. The inner cylindrical portion may include a ridge on an outer surface thereof configured for selective engagement with an actuator clip of the knife assembly. The actuator clip may include an inner surface configured for selectively engaging the ridge on the outer surface of the inner cylindrical portion. The actuator clip may include an outer surface configured for selectively engaging a groove on an inner surface of the pusher. The pusher and the knife assembly may be substantially cylindrical.

Also provided is a method of stapling tissue. The method includes providing a surgical stapling instrument having a pusher and a knife assembly. The knife assembly is selectively fixed relative to the pusher for independent movement relative to the pusher. The method further includes advancing the pusher to cause the ejection and forming of staples, retracting the pusher and re-advancing the pusher to cause the advancement of the knife assembly and the cutting of tissue. The method may further include providing a lapse of time between the ejection/forming of the staples and the cutting of tissue to allow for tissue benefit or normalization. The retracting of the pusher may include retracting the pusher to a location proximal of the initial location. The knife assembly may include an actuator clip for selectively engaging the pusher.

DESCRIPTION OF THE DRAWINGS

Embodiments of a surgical stapling instrument including a cartridge assembly that is actuated independently from actuation of the cutting assembly are disclosed herein with reference to the drawings, wherein:

FIG. 10 is a cross-sectional side view of the cartridge assembly of FIG. 3, in an initial position;

FIG. 11 is a cross-sectional perspective view of the cartridge assembly of FIG. 10 in the initial position;

FIG. 12 is an enlarged sectional view of the indicated area of detail of FIG. 11;

FIG. 14 is a cross-sectional perspective view of the cartridge assembly of FIGS. 10 and 11, with the pusher in a retracted position;

FIG. 15 is an enlarged sectional view of the indicated area of detail of FIG. 14;

FIG. 17 is a cross-sectional perspective view of the cartridge assembly of FIGS. 10 and 11, upon completion of the tissue cutting stroke;

FIG. 18 is an enlarged sectional view of the indicated area of detail of FIG. 17;

FIG. 27 is a left side, perspective view of the first and second drive converter of the adapter assembly of FIGS. 24-26;

FIG. 28 is an enlarged perspective view of a distal end of the first and second drive converters of the adapter of FIGS. 24-26, illustrating the operation of the first drive converter;

FIG. 29 is a right side, perspective view of a first and second drive converter of the adapter assembly of FIGS. 24-26; and FIG. 30 is an enlarged perspective view of a distal end of the first and second drive converters of the adapter assembly of FIGS. 24-26, illustrating the operation of the second drive converter.

DETAILED DESCRIPTION

Embodiments of the presently disclosed circular stapling instrument including independently actuated staple forming and cutting strokes will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
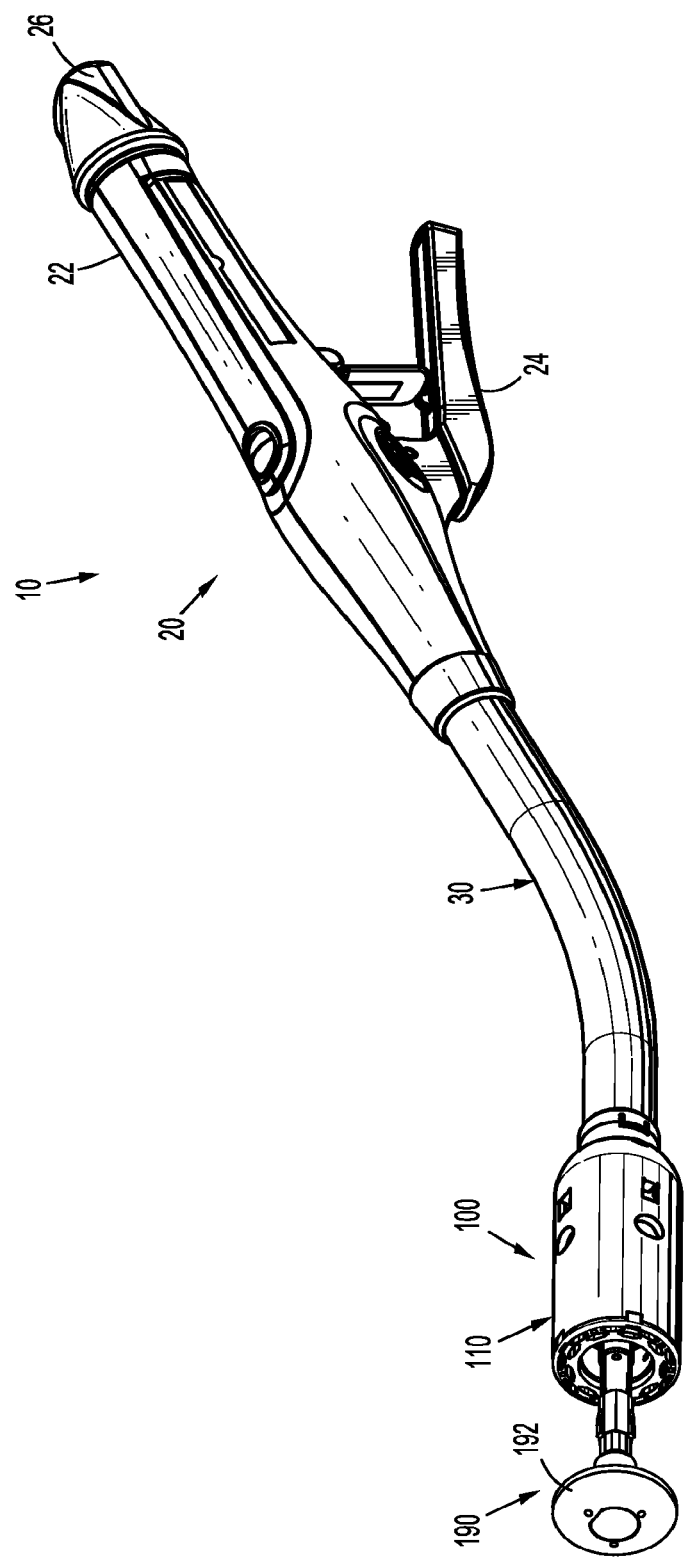
FIG. 1 is a perspective view of a surgical stapling instrument including a cartridge assembly according to an embodiment of the present disclosure.

FIG. 1 illustrates an embodiment of a circular stapling instrument according to the present disclosure, shown generally as circular stapler 10. Circular stapler 10 includes a handle assembly 20 and an elongate body 30 extending distally from handle assembly 20. A tool assembly 100 is mounted on a distal end of elongate body 30. Handle assembly 20 includes a fixed handle 22 and a moveable handle or trigger 24. Handle assembly 20 also includes an adjustment knob 26 for moving anvil assembly 190 relative to cartridge assembly 110. The structure and function of handle assembly 20 will only be described herein to the extent necessary to fully disclose the operation of tool assembly 100. It is envisioned that tool assembly 100 may be modified for use with any actuation assembly capable of advancing a drive member for a first function, and retracting and re-advancing the drive member for a second function. Alternatively, the actuation mechanism may have a first drive member for performing a first function and a second drive member for performing a second function.

Figure 2:
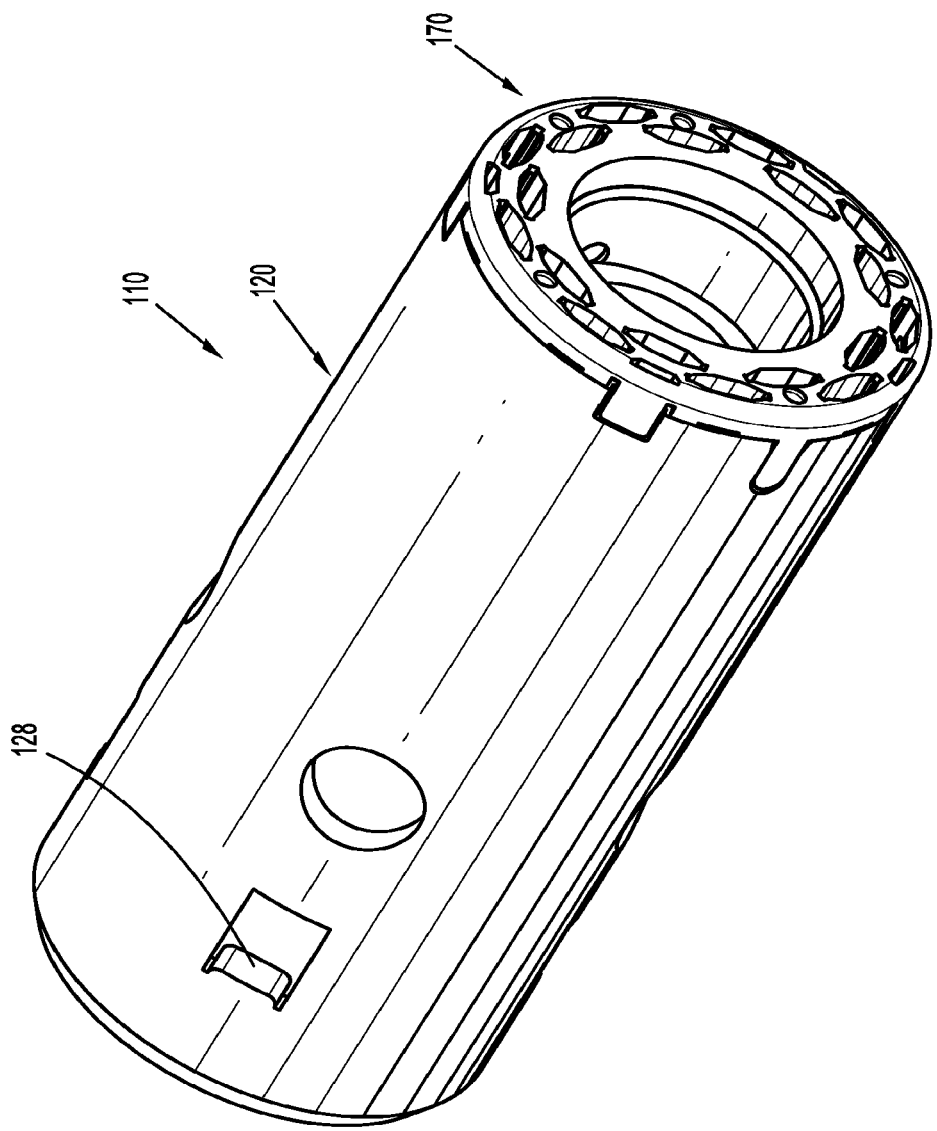
FIG. 2 is an enlarged perspective view of the cartridge assembly of the surgical stapling instrument of FIG. 1.

With reference to FIGS. 1 and 2, cartridge assembly 110 of tool assembly 100 is operably mounted to a distal end of elongate body 30 of circular stapler 10. In one embodiment, cartridge assembly 110 is removably secured to elongate body 30 such that cartridge assembly 110 may be replaced and circular stapler 10 may be reused. Alternatively, circular stapler 10 is configured for a single use, i.e., disposable.

Figure 3:
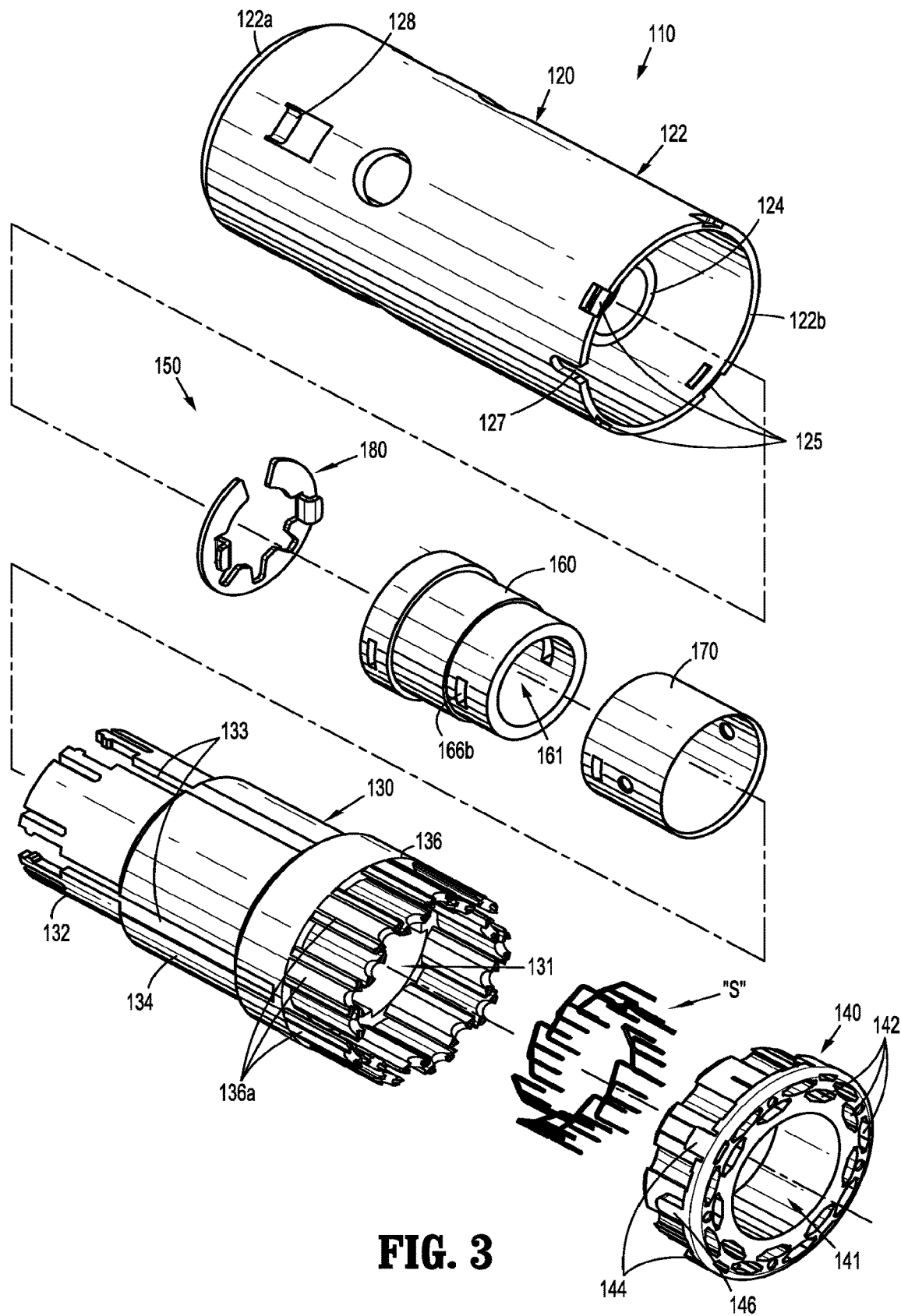
FIG. 3 is an exploded perspective view of the cartridge assembly of FIG. 2.

With reference to FIGS. 3 and 11, cartridge assembly 110 includes a housing 120, a pusher member 130, a staple cartridge 140, and a knife assembly 150. Housing 120 of cartridge assembly 110 includes an outer cylindrical portion 122, an inner cylindrical portion 124 and a plurality of radially extending supports or ribs 126 extending between inner cylindrical portion 124 and outer cylindrical portion 122. Inner cylindrical portion 124 and outer cylindrical portion 122 are coaxial and define a recess 123 therebetween configured to receive a distal portion of pusher 130 and knife assembly 150. As will be discussed in further detail below, inner cylindrical portion 124 of housing 120 includes a ridge 124a (FIG. 12) extending about an outer surface thereof configured to prevent advancement of knife assembly 150 during a first or staple forming stroke of circular stapler 10. A proximal end 122a of outer cylindrical portion 122 of housing 120 includes a tab 128 configured to operably engage cartridge assembly 110 to a distal end of elongate body 30. A distal end 122b of outer cylindrical portion 122 of housing 120 defines a plurality of recesses 125 formed thereabout configured to receive mounting tabs 144 of staple cartridge 140. Distal end 122b of outer cylindrical portion 122 of housing 120 also defines a slot 127 configured to receive a projection 146 formed on staple cartridge 140. Slot 127 is positioned such that when projection 146 is received in slot 127, mounting tabs 144 of staple cartridge 140 are properly aligned with recesses 125.

With continued reference to FIG. 3, pusher 130 is a substantially cylindrical member including a proximal portion 132, a middle portion 134, and a distal portion 136. Proximal portion 132 of pusher 130 is configured for operable engagement with a drive member (not shown). Distal portion 136 of pusher 130 includes a plurality of pusher members 136a arranged in two concentric rows. Pusher members 136a align with staples "S" received within staple cartridge 140 such that advancement of pusher 130 relative to staple cartridge 140 causes ejection of staples "S" from staple cartridge 140.

Pusher 130 defines a longitudinal passage 131 extending therethrough. A distal end of longitudinal passage 131 is sized and configured to receive knife assembly 150 in a selectively slidable manner.

Pusher 130 further defines a plurality of longitudinal slots 133 extending the length of proximal and middle portion 132, 134. Slots 133 correspond in number and location to supports 126 formed between and interconnecting outer and inner cylindrical portions 122, 124 of housing 120. In this manner, pusher 130 is configured to be received within outer cylindrical portion 122 of housing 120 and about inner cylindrical portion 124 of housing 120 as supports 126 are received within slots 133.

Figure 9:
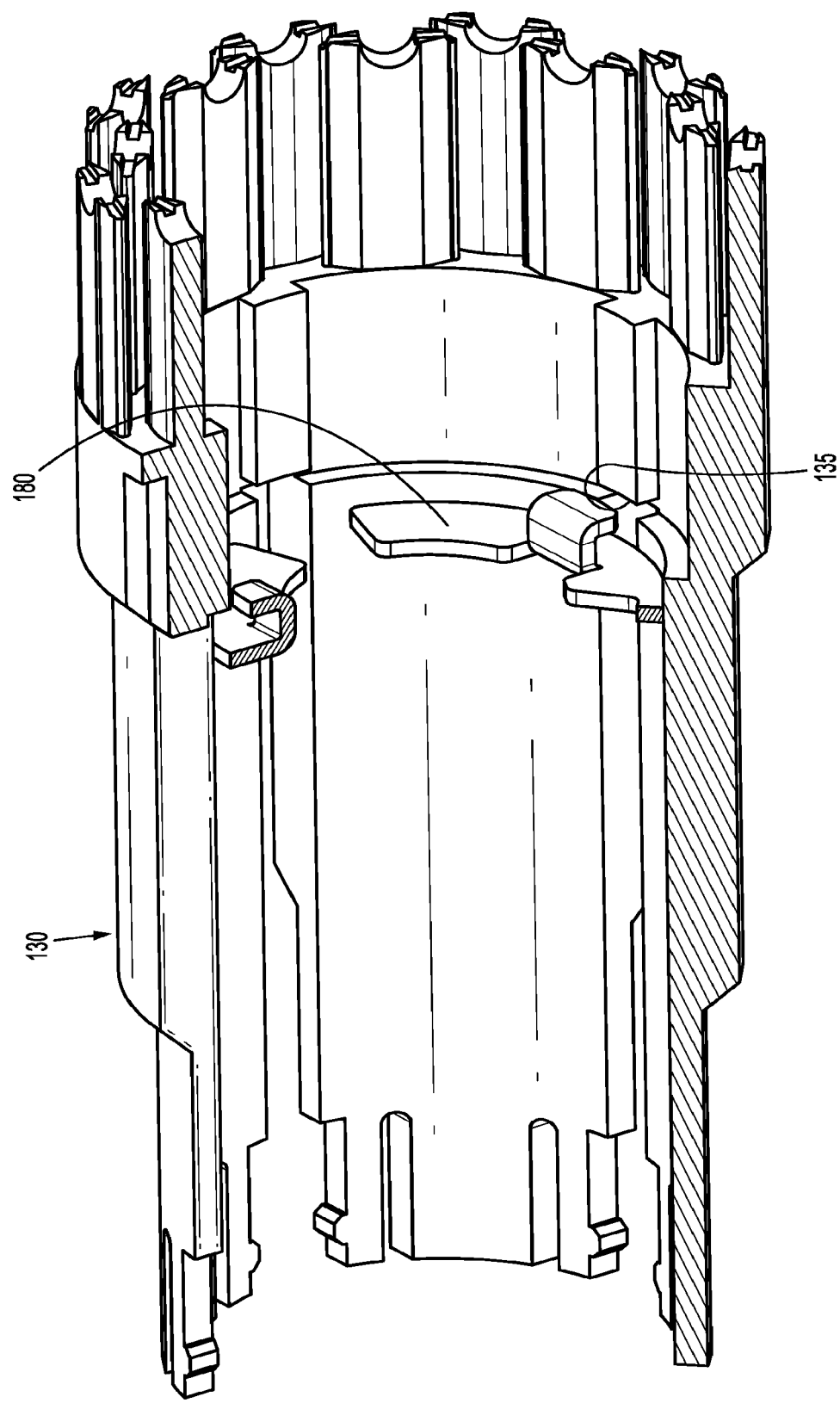
FIG. 9 is a cross-sectional side view of the pusher and the actuator clip of the cartridge assembly of FIG. 3, with the actuator clip in a compressed condition.

Pusher 130 also defines a groove 135 (FIG. 9) extending about an inner surface thereof between middle and distal portions 134, 136. As will be discussed in further detail below, groove 135 is configured to permit the operable engagement of knife assembly 150 with pusher 130.

With reference to FIGS. 2 and 3, staple cartridge 140 includes a substantially cylindrical member configured to operably engage a distal end 122b of outer cylindrical portion 122 of housing 120 and defines a longitudinal opening 141 configured to receive knife assembly 150 therethrough. Staple cartridge 140 includes a plurality of staple receiving pockets 142 disposed about opening 141 arranged in two concentric rows. Staple receiving pockets 142 align with pusher members 136a formed on distal portion 136 of pusher 130. As discussed above, staple cartridge 140 also includes a plurality of mounting tabs 144 and a protrusion 146. Mounting tabs 144 operably engage recesses 125 formed on distal end 122b of outer cylindrical portion 122 of housing 120 while protrusion 146 assures the proper alignment of staple cartridge 140 with housing 120.

Figure 4:
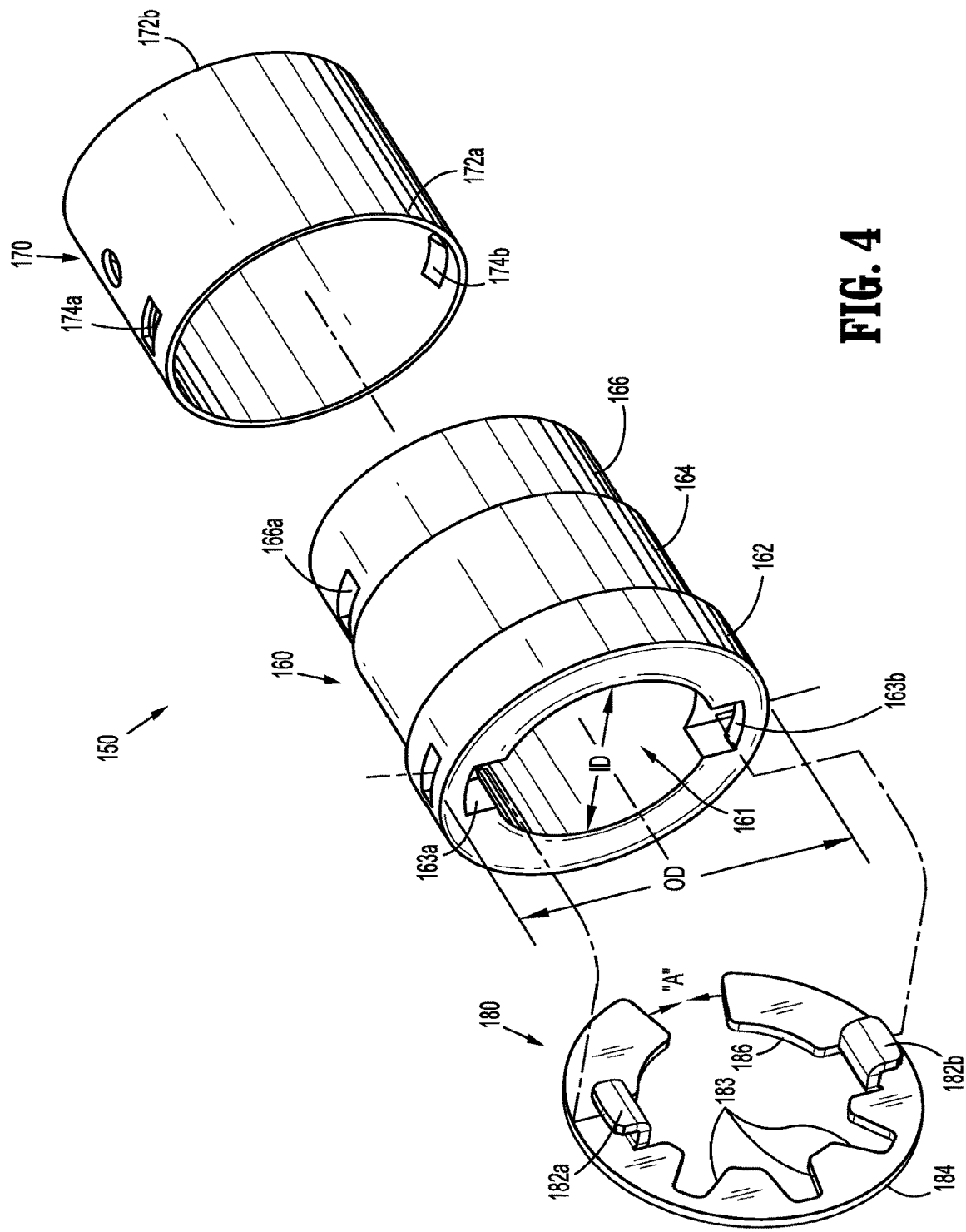
FIG. 4 is an exploded view of a knife assembly of the cartridge assembly of FIGS. 2 and 3.

With reference now to FIGS. 3-8, knife assembly 150 includes an actuator member 160, a circular knife 170 and an actuator clip 180. With particular reference to FIG. 4, actuator member 160 is substantially cylindrical and includes a proximal portion 162, a middle portion 164 and a distal portion 166. Actuator member 160 defines a longitudinal passage 161 extending therethrough. Longitudinal passage 161 is sized and dimensioned to be received about a distal end of inner cylindrical portion 124 of housing 120. Proximal portion 162 of actuator member 160 includes a pair of opposed notches 163a, 163b. As will be discussed in further detail below, notches 163a, 163b are configured to receive flanges 182a, 182b, respectively, of actuator clip 180. Distal portion 166 of actuator member 160 is configured to receive knife 170 thereabout and defines a pair of recesses 166a, 166b configured to engage respective locking tabs 174a, 174b formed on or projecting from knife 170.

With particular reference still to FIG. 4, knife 170 includes a substantially cylindrical member having proximal and distal ends 172a, 172b Knife 170 is sized and dimensioned to be received through longitudinal opening 141 of staple cartridge 140. Distal end 172b of knife 170 includes a sharpened surface defining a knife edge configured for cutting tissue. As discussed above, proximal end 172a of knife 170 is configured to be received about distal portion 166 of knife actuator 160 and includes a pair of tabs 174a, 174b configured to be received within respective recesses 166a, 166b formed in distal portion 166 of knife actuator 160 to secure knife 170 to knife actuator 160.

Still referring to FIG. 4, actuator clip 180 is a substantially C-shaped member including a pair of opposed flanges 182a, 182b. Flanges 182a, 182b are configured to be received within respective notches 163a, 163b formed in proximal portion 162 of knife actuator 160. Actuator clip 180 includes an outer portion 184 and an inner portion 186. Inner portion 186 defines a plurality of cutouts 183. Cutouts 183 permit the compression of actuator clip 180, as indicated by arrows "A".

Figure 5:
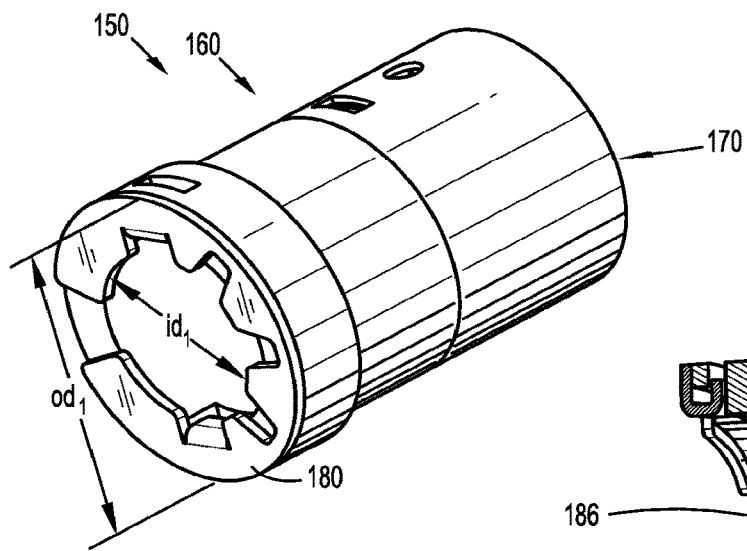
FIG. 5 is a perspective view of the knife assembly of FIG. 4, with the actuator clip in a compressed condition.
Figure 6:
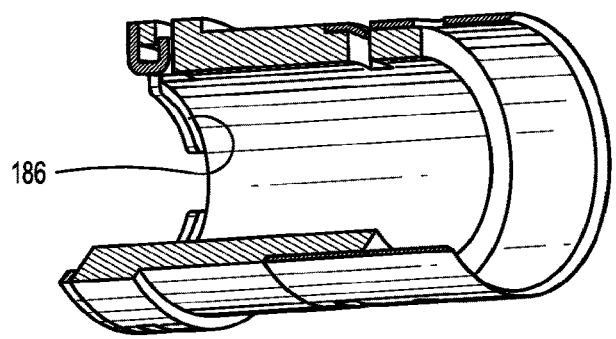
FIG. 6 is a cross-section view of the knife assembly of FIG. 5.

When in a compressed condition, as seen in FIGS. 5 and 6, actuator clip 180 includes an inner diameter "$id_1$" and an outer diameter "$od_1$". Inner diameter "$id_1$" of actuator clip 180 measures less then an inner diameter "ID" (FIG. 4) of proximal portion 162 of actuator member 160 which is fixed. As will be discussed in further detail below, in this manner, when actuator clip 180 is received about inner cylindrical portion 124 of housing 120, inner portion 186 of actuator clip 180 engages ridge 124a formed on the outer surface of inner cylindrical portion 124 to maintain knife assembly 150 fixed relative to housing 120. Outer diameter "$od_1$" of actuator clip 180 measures less then or equal to an outer diameter "OD" (FIG. 4) of proximal portion 162 of actuator member 160 which is fixed. As also will be discussed in further detail below, in this manner, knife assembly 150 is configured to permit the longitudinal advancement and retraction of pusher 130 relative thereto during the first or staple forming stroke.

Figure 7:
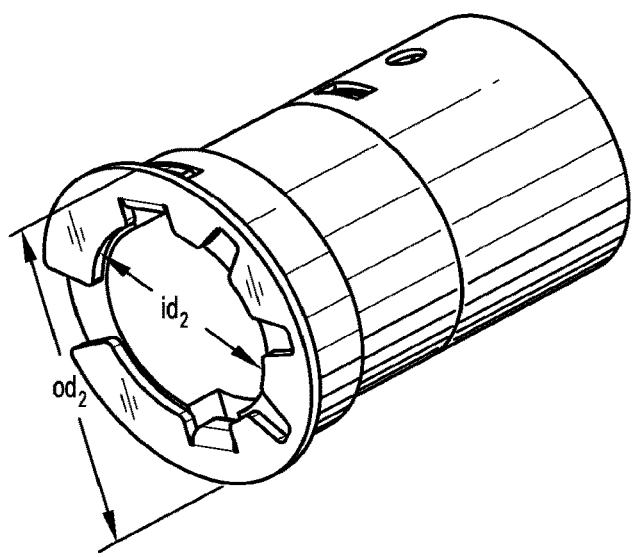
FIG. 7 is a perspective view of the knife assembly of FIG. 4, with the actuator clip in an uncompressed condition.
Figure 8:
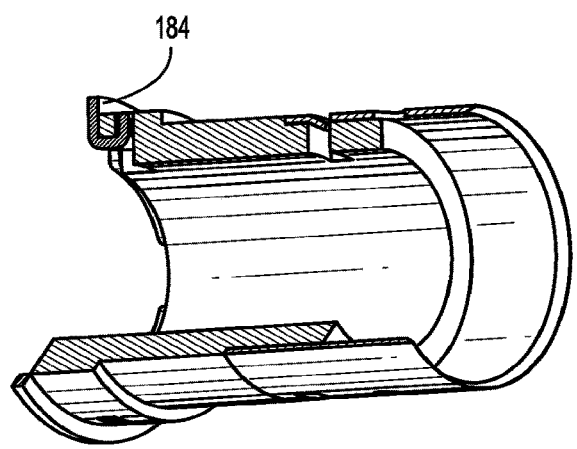
FIG. 8 is a cross-sectional side view of the knife assembly of FIG. 5.

In a non-compressed condition, as seen in FIGS. 7 and 8, actuator clip 180 includes an inner diameter "$id_2$" and an outer diameter "$od_2$". Inner diameter "$id_2$" of actuator clip 180 measures less than or equal to inner diameter "ID" (FIG. 4) of proximal portion 162 of actuator member 160. As will be discussed in further detail below, in this manner, when actuator clip 180 transitions from the compressed condition (FIGS. 5 and 6) to the non-compressed condition (FIGS. 7 and 8), inner portion 186 of actuator clip 180 disengages ridge 124a formed on the outer surface of inner cylindrical portion 124. Outer diameter "$od_2$" of actuator clip 180 measures greater than outer diameter "OD" (FIG. 4) of proximal portion 162 of actuator member 160. As also will be discussed in further detail below, in this manner, when pusher 130 is retracted following the first or staple forming stroke, pusher 130 is retracted sufficiently to align groove 135 formed on the inner surface of pusher 130 with actuator clip 180, actuator clip 180 is permitted to expand such that outer portion 184 of actuator clip 180 engages groove 135 to lock knife assembly 150 relative to pusher 130.

The operation of cartridge assembly 110 will now be described with reference to FIGS. 9-18. Referring initially to FIGS. 9-12, cartridge assembly 110 is shown in an initial, or pre-fired condition. In the initial condition, pusher 130 is disposed between outer and inner cylindrical portions 122, 124 of housing 120 and within recess 123. Knife assembly 150 is received within longitudinal passage 131 of pusher 130 and about a distal portion of inner cylindrical portion 124 of housing 120. Staple cartridge 140 operably engages distal end 122b of outer cylindrical portion 122 of housing 120 to operably retain pusher 130 and knife assembly 150 within housing 120. Pusher 130 is positioned such that actuator clip 180 of knife assembly 150 is located proximal of groove 135 formed in the inner surface of pusher 130. The proximal position of actuator clip 180, relative to groove 135 formed in pusher 130, maintains actuator clip 180 in the compressed condition and the engagement of inner portion 186 of actuator clip 180 with ridge 124a formed in the outer surface of inner cylindrical portion 124 of housing 120 permits longitudinal movement of pusher 130 relative to knife assembly 150.

Figure 13:
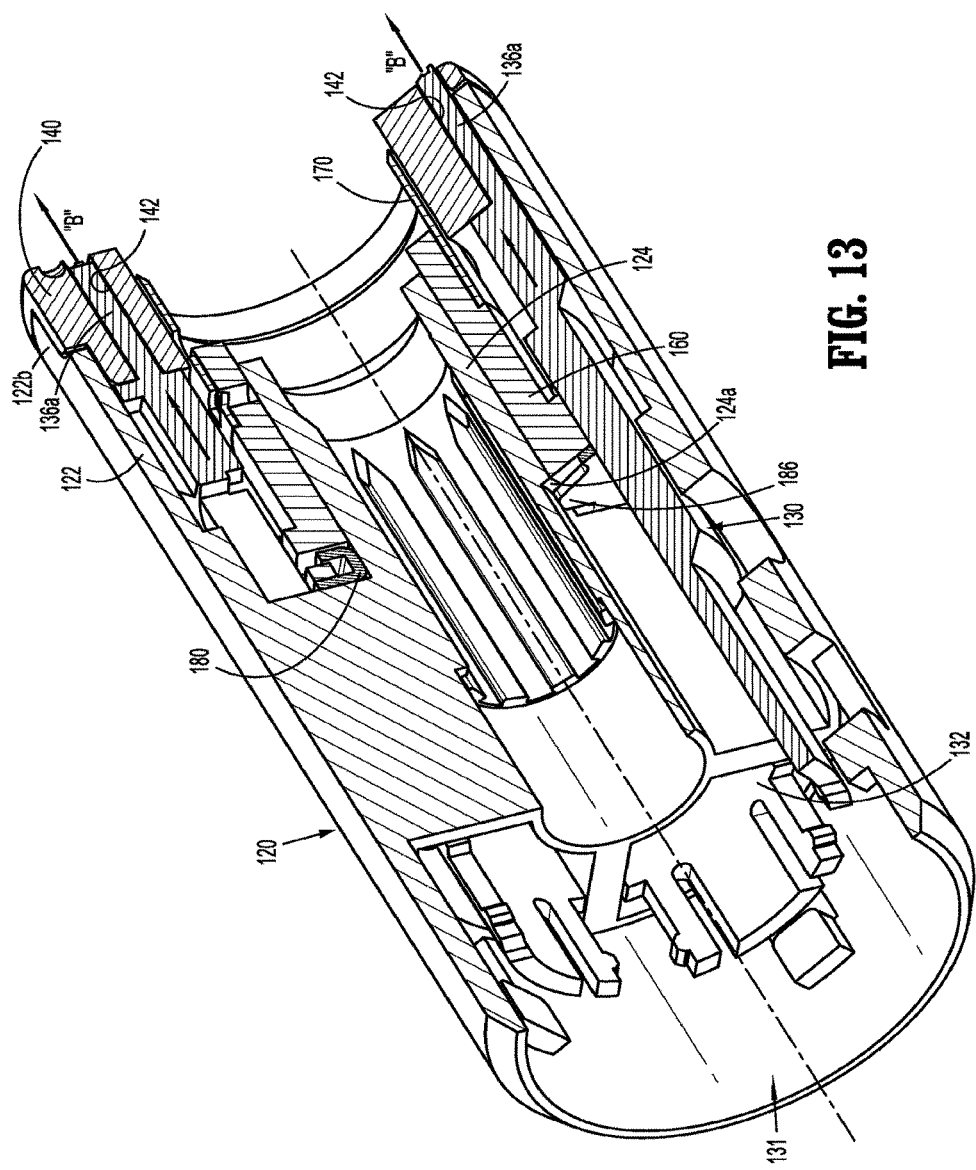
FIG. 13 is a cross-sectional perspective view of the cartridge assembly of FIGS. 10 and 11, upon completion of the stapling stroke.

With reference now to FIG. 13, during the first or staple forming stroke of circular stapler 10 (FIG. 1), following approximation of anvil 192 against cartridge assembly 110, retraction or actuation of trigger 24 relative to fixed handle 22 causes advancement of a drive assembly (not shown) which operably engages proximal portion 132 of pusher 130 to cause the advancement of pusher 130, as indicated by arrows "B". Advancement of pusher 130 causes pusher members 136a on distal portion 136 thereof to be advanced into staple receiving pockets 142 of staple cartridge 140 and to eject staples "S" from staple cartridge 140. Although not show, the ejection of staples "S" from staple cartridge 140 causes advancement of staples "S" into anvil 192 of anvil assembly 190 (FIG. 10). As staples "S" are advanced into anvil 192, staples "S" are formed to secure the tissue retained between anvil 192 and staple cartridge 140. Knife assembly 150 is maintained in a fixed position relative to inner cylindrical portion 124 of housing 120 during the forming of staples "S" because of engagement of inner portion 186 of actuator clip 180 with ridge 124a formed on inner cylindrical portion 124.

Figure 16:
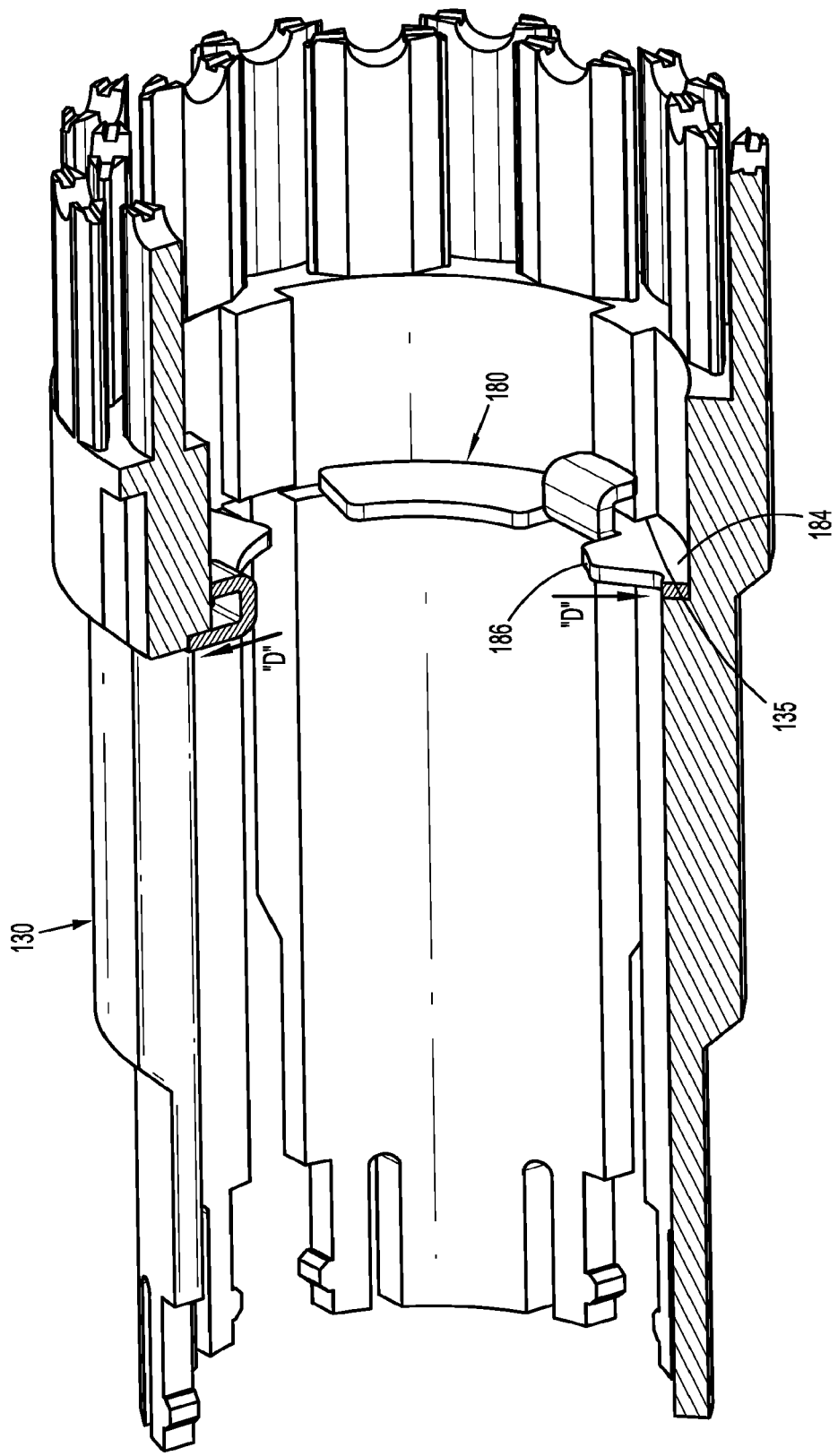
FIG. 16 is a cross-sectional side view of the pusher and actuator clip of FIG. 9, with the actuator clip in an uncompressed condition.
Figure 19:
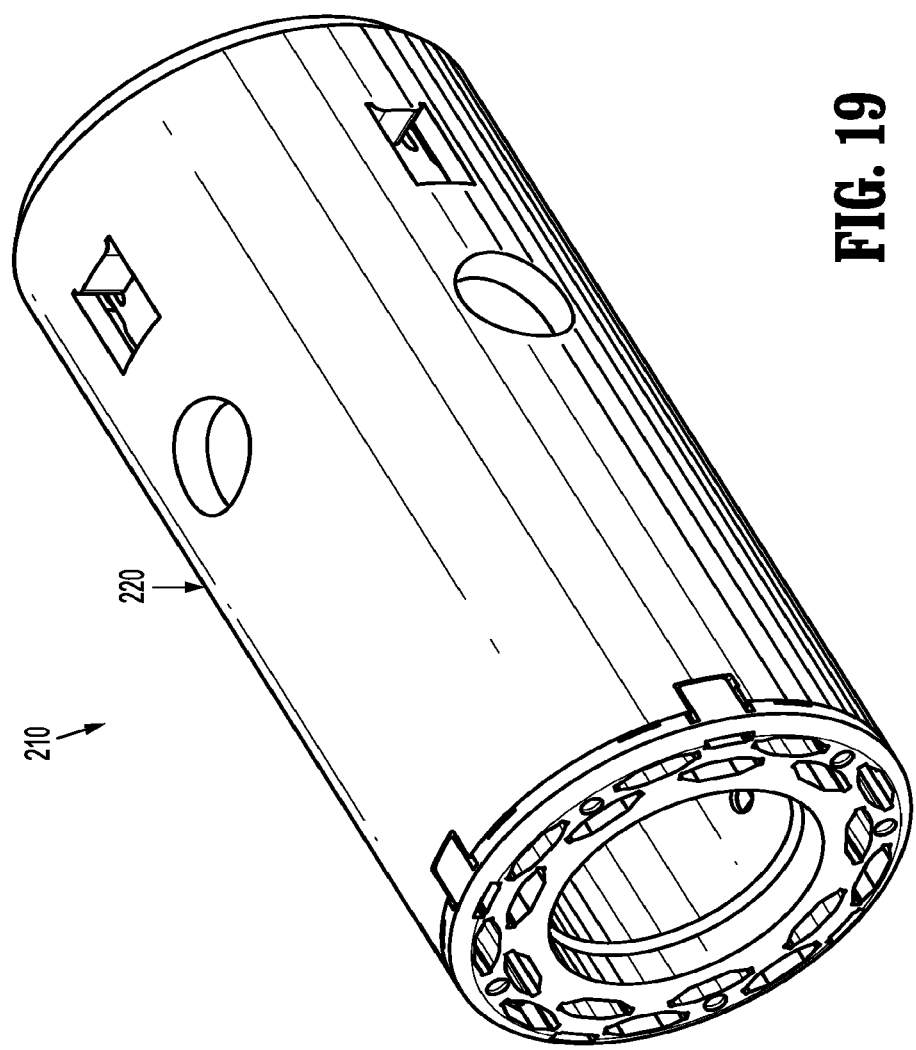
FIG. 19 is a perspective view of a cartridge assembly according to another embodiment of the present disclosure.

With reference to FIGS. 14-16, upon completion of the firing stroke, pusher 130 is retracted proximally relative to housing 120, as indicated by arrows "C", to a position proximal of its initial position prior to the staple forming stroke. Pusher 130 is sufficiently retracted relative to knife assembly 150 such that groove 135 formed on the inner surface of pusher 130 aligns with actuator clip 180. In this manner, actuator clip 180 is no longer maintained in the compressed condition by the inner surface of pusher 130 and is permitted to decompress to a non-compressed condition, as indicated by arrows "D" (FIG. 16). Decompression of actuator clip 180 causes outer portion 184 of actuator clip 180 to engage groove 135 of pusher 130, thereby locking knife assembly 150 relative to pusher 130. Decompression of actuator clip 180 also causes the disengagement of inner portion 186 of actuator clip 180 from ridge 124a formed on the outer surface of inner cylindrical portion 124 of housing 120. In this manner, knife assembly 150 is no longer locked relative to inner cylindrical portion 124 of housing 120.

With reference now to FIGS. 17 and 18, during the second or cutting stroke of circular stapler 10 (FIG. 1), refraction or actuation of trigger 24 relative to handle 26 causes advancement of the drive assembly (not shown) which operably engages pusher 130 to cause the advancement of pusher 130, as indicated by arrows "E" (FIG. 18). Since knife assembly 150 is locked relative to pusher 130 through receipt of outer portion 184 of actuator clip 180 in groove 135 of pusher 130 (as describe above), advancement of pusher 130 also causes the advancement of knife assembly 150, as indicated by arrows "F". Advancement of knife assembly 150 relative to staple cartridge 140 causes knife 170 to be received through longitudinal opening 141 of staple cartridge 140, thereby severing the tissue retained between anvil 192 and a distal end of staple cartridge 140. Retraction of the drive assembly (not shown) causes the retraction of pusher 130 and knife assembly 150.

The use of circular stapler 10 will now be described with reference to the figures. In use, circular stapler 10 is operated in a manner substantially similar to a traditional circular stapler. Once oriented such that the tissue to be stapled is received between cartridge assembly 110 and anvil assembly 190, and anvil assembly 190 is approximated against cartridge assembly 110, trigger 24 is squeezed to cause the actuation of handle assembly 20. As discussed above, actuation of handle assembly 20 causes a first advancement of a drive assembly (not shown) which causes the advancement of pusher 130. During the first or staple forming stroke, pusher 130 is moved relative to housing 120. Because knife assembly 150 is selectively fixed to inner cylindrical portion 124, pusher 130 also moves relative to knife assembly 150. In this manner, only the staple forming function is performed during the first stroke. Therefore, the force required for completion of the first stroke of circular stapler 10 does not include the force necessary to advance knife 170 through the tissue retained between anvil assembly 190 and cartridge assembly 110.

Upon completion of the first or staple forming stroke, in one embodiment, trigger 24 is released to permit the retraction of the drive member and pusher 130. In other embodiments, the drive member may automatically retract upon completion of the first stroke. As discussed above, pusher 130 is retracted to a position proximal of its initial position to align actuator clip 180 with groove 135 formed in the inner surface of pusher 130. The retraction of pusher 130 causes engagement of actuator clip 180 with pusher 130, thereby locking knife assembly 150 relative to pusher 130.

A subsequent squeezing or actuation of trigger 124 causes a second advancement of the drive member and pusher 130. Since knife assembly 150 is now locked relative to pusher 130, advancement of pusher 130 also advances knife assembly 150. Advancement of knife assembly 150 causes the cutting of the tissue retained between cartridge assembly 110 and anvil assembly 190. Because staples "S" were ejected and formed during the first stroke of circular stapler 10, the force required to complete the second or cutting stroke of circular stapler 10 is less then the force necessary to complete both the staple ejecting/forming and tissue cutting functions.

In addition to the reduced force requirements provided by the two stroke operation of circular stapler 10, the independent or decoupled staple forming and tissue cutting function of circular stapler 10 also permits the varying of the staple crimp height relative to the knife travel distance, the varying of the staple travel speed relative to the knife travel speed, and provides the addition of a dwell time between staple formation and tissue cutting. This configuration allows a clinician to optimize staple crimp heights to given conditions, such as, tissue thickness, tissue compliance and clamping force. This configuration may also allow for the monitoring of staple forming and knife cutting forces to alert the clinician in case an abnormal force is detected. This configuration further allows force and other data to be monitored and used for data collection and research, which when analyzed, may lead to further optimization of operational parameters, such as staple crimp height, dwell time and/or travel speed. By independently controlling and optimizing these various stapling and cutting parameters, improved hemostasis and/or anastomonic joint strength may result across a much broader range of tissue thicknesses, thereby allowing a clinician to have improved and customized control over the results.

With reference to FIGS. 19-23, in an alternative embodiment of the present disclosure, cartridge assembly 210 is configured for engagement with an actuator assembly having a first drive member (not shown) and a second drive member (not shown). Each of first and second drive members may be individually actuated by the same actuation assembly or may instead by actuated by the same actuation assembly during subsequent actuation strokes.

Figure 20:
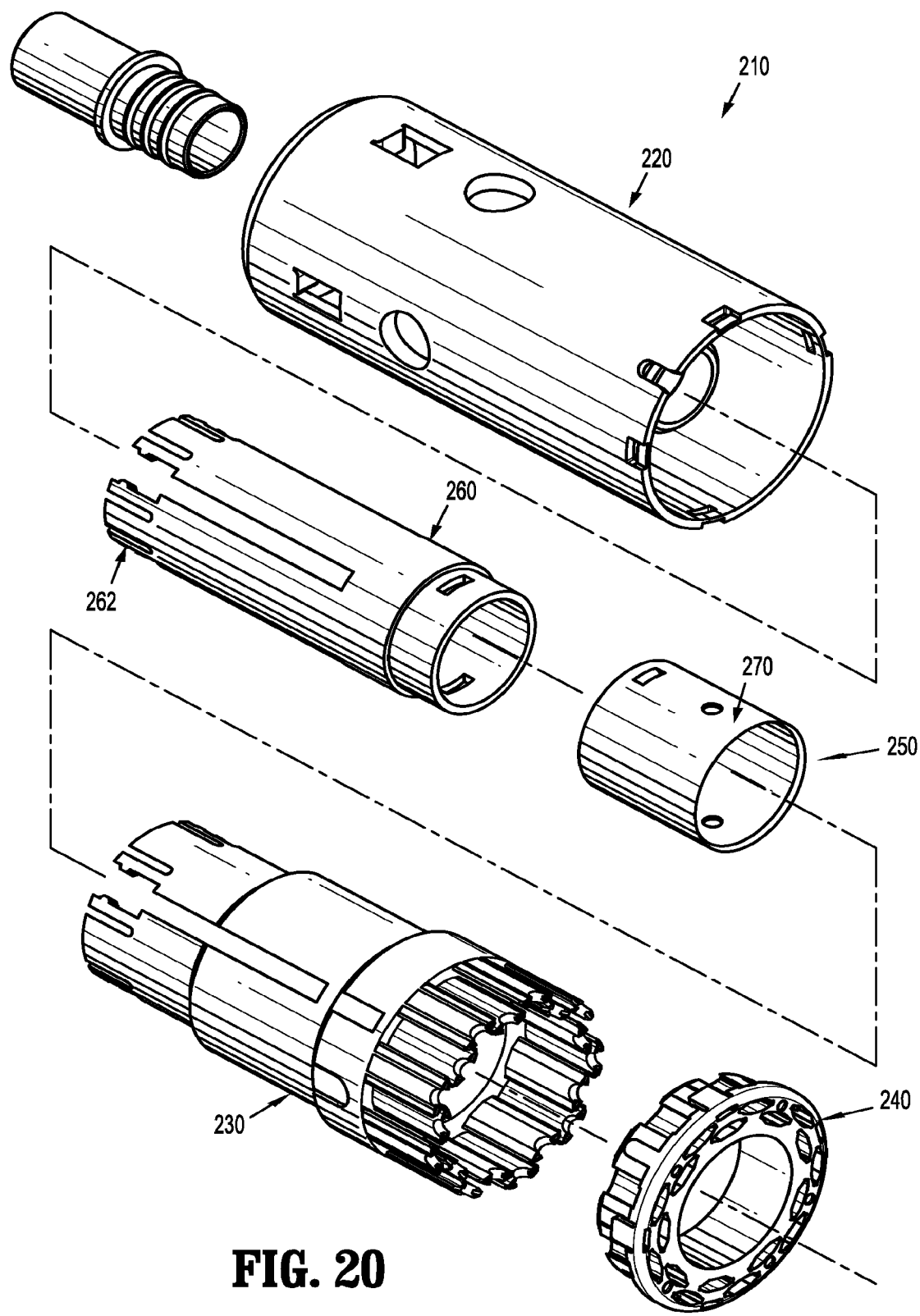
FIG. 20 is an exploded perspective view of the cartridge assembly of FIG. 19.
Figure 21:
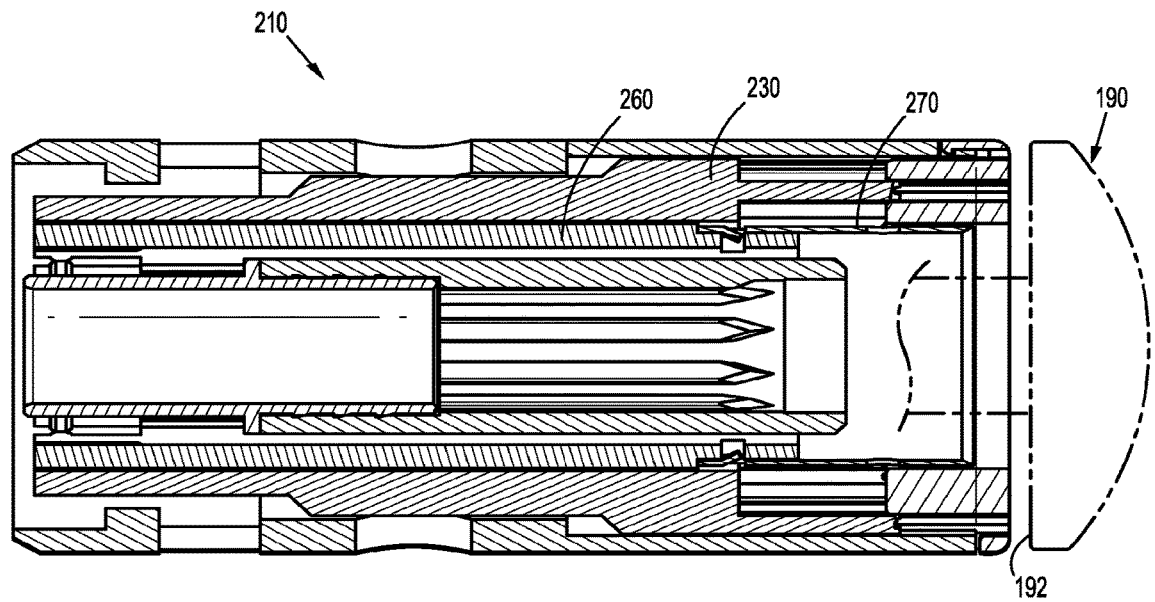
FIG. 21 is a cross-sectional side view of the cartridge assembly of FIGS. 19 and 20, in an initial position.
Figure 22:
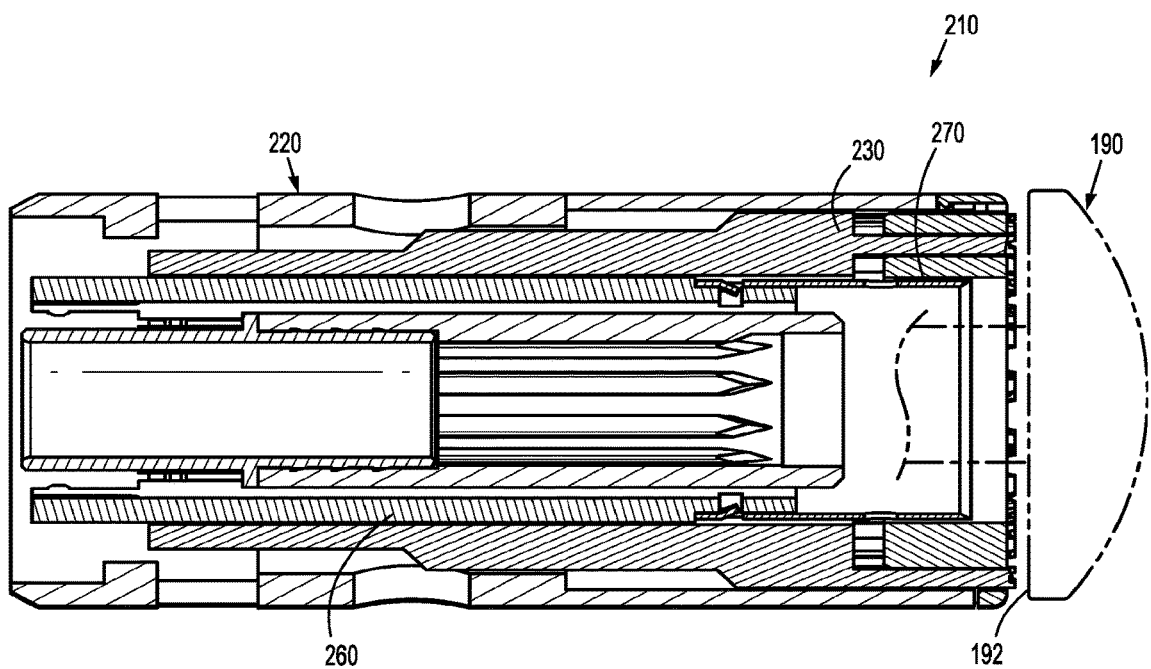
FIG. 22 is a cross-sectional side view of the cartridge assembly of FIGS. 19-21, upon completion of the stapling stroke.
Figure 23:
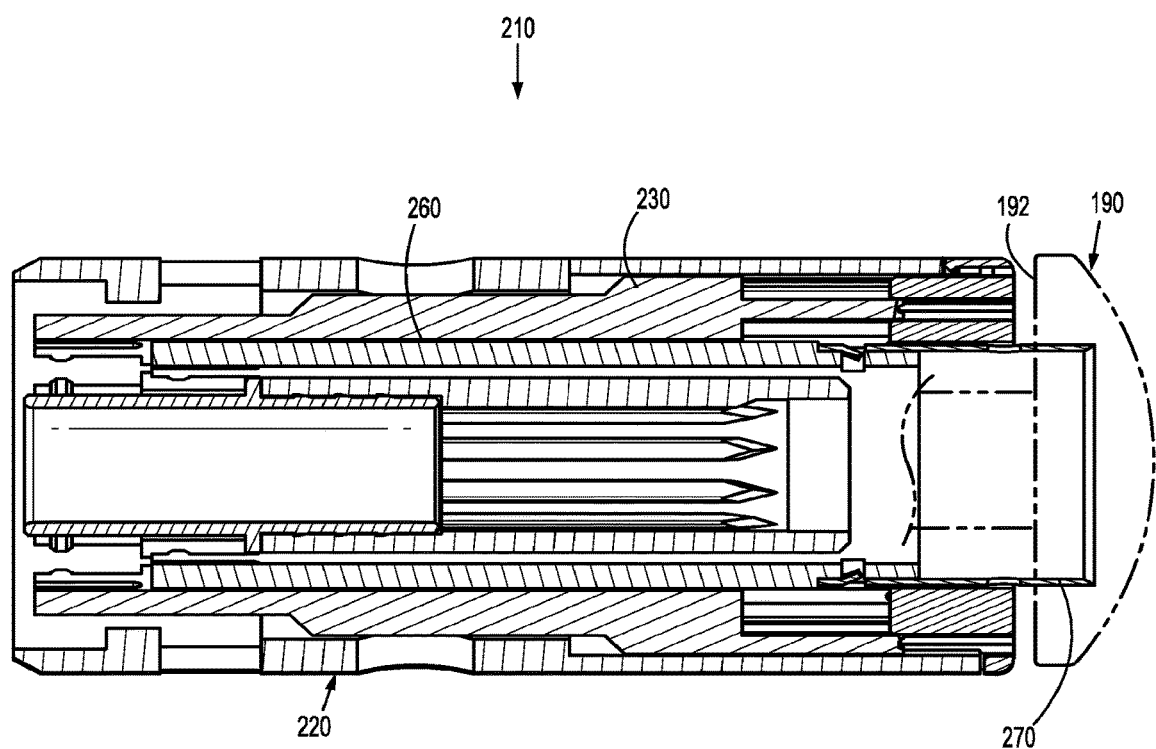
FIG. 23 is a cross-sectional side view of the cartridge assembly of FIGS. 19-22, upon completion of the tissue cutting stroke.
Figure 24:
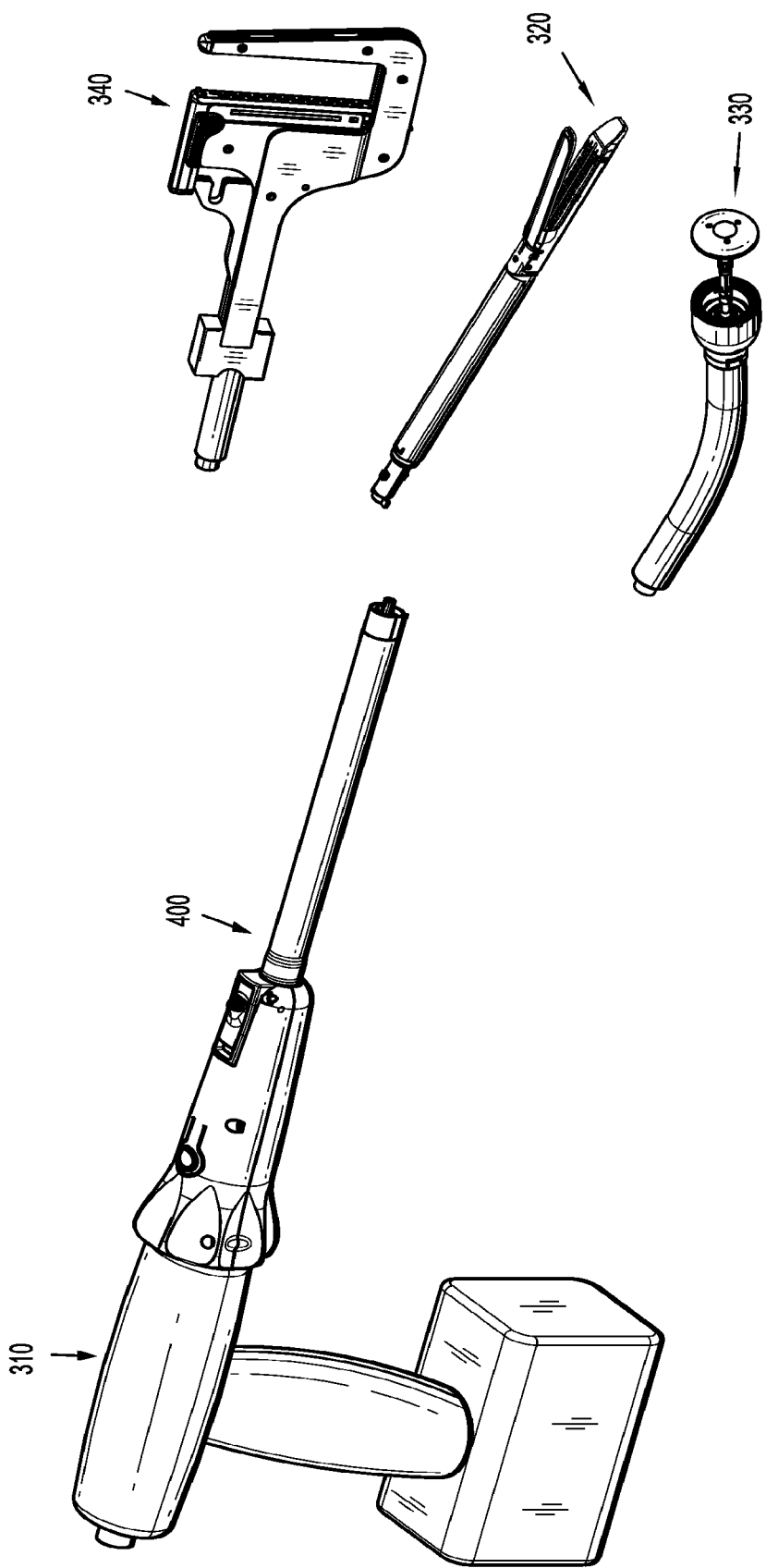
FIG. 24 is a perspective view of a surgical device including powered actuator assembly including first and second drive members, illustrating the potential use with various end effectors.
Figure 25:
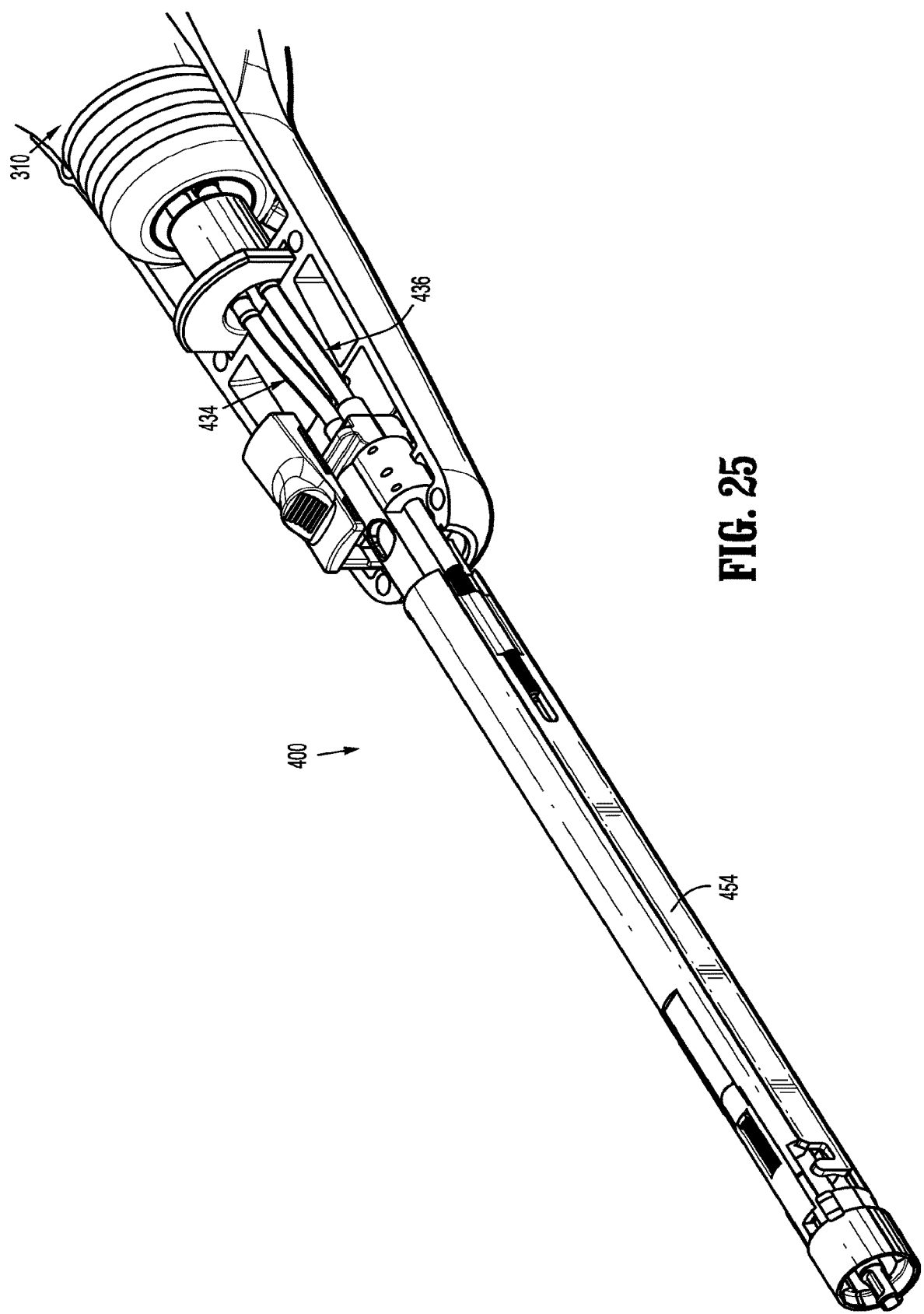
FIG. 25 is an enlarged perspective view of the adapter assembly of FIG. 24.

With particular reference to FIG. 20, cartridge assembly 210 is substantially similar to cartridge assembly 110 and will only be described as relates to the differences therebetween. Cartridge assembly 210 includes a housing 220, a pusher 230, a staple cartridge 240, and a knife assembly 250. Knife assembly 250 includes an actuator member 260 and a knife 270. Unlike knife assembly 150 of cartridge assembly 110, knife assembly 250 does not include an actuator clip. Instead actuator member 260 includes a proximal portion 262 configured to operably engage the second drive member (not shown).

Cartridge assembly 210 operates in a manner similar to cartridge assembly 110. During a first or staple forming stroke, pusher 230 is advanced relative to housing 220 to cause the ejection of staples "S" from staple cartridge 240. Ejected staples "S" are deformed against an anvil 192 of anvil assembly 190. During the first stroke, knife assembly 250 is maintained in a fixed position relative to housing 220. During the second or tissue cutting stroke, knife assembly 250 is advanced relative to housing 220 to cause the cutting of the tissue retained between anvil assembly 190 and staple cartridge 240. As discussed above, the staple forming stroke and the tissue cutting stroke may be caused by the same or different actuators.

Figure 26:
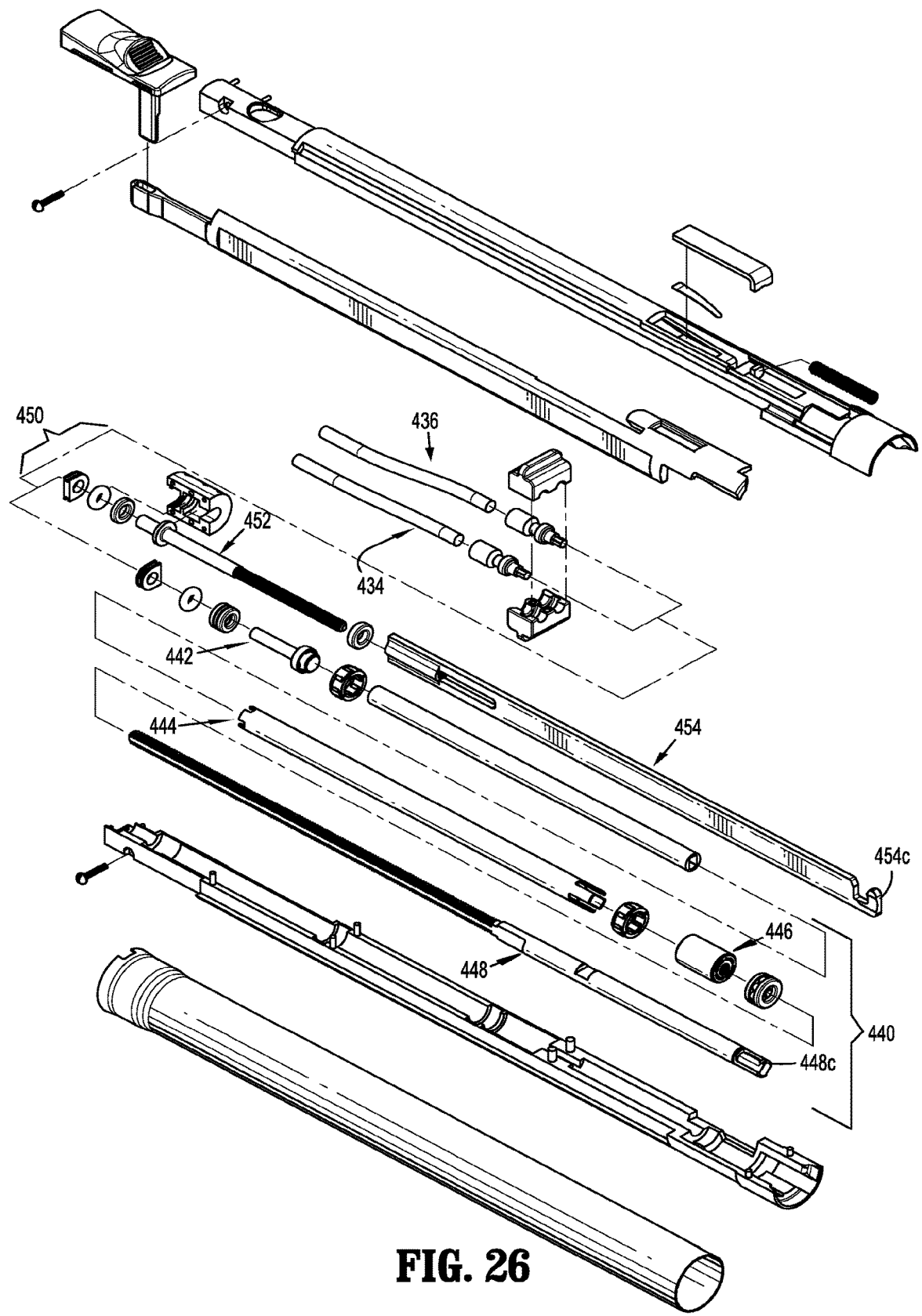
FIG. 26 is an exploded perspective view of a distal end of the adapter assembly of FIG. 25.

Commonly owned U.S. patent application Ser. No. 12/946,082, filed Nov. 15, 2010, the content of which is incorporated herein in its entirety, discloses a surgical device having a powered actuator assembly including first and second drive members. Briefly, and with reference to FIGS. 24-30, surgical device 310 includes an adapter assembly 400. Adapter 400 includes a first flexible drive cable 434 connected to a first proximal drive shaft 414, and a second flexible drive cable 436 connected to a second proximal drive shaft 416. As either of first and/or second proximal drive shafts 414, 416 is/are rotated, the rotation is transmitted to respective first and/or second flexible drive cables 434, 436. Referring to FIG. 26, first flexible drive cable 434 is connected to first drive converter assembly 440, and second drive cable 436 is connected to second drive converter assembly 450. Turning to FIGS. 27 and 28, as a coupling nut 446 of first drive converter assembly 440 is rotated (in the direction of arrow "G") due to a rotation of a tubular sleeve 444, a proximal coupling 442, a first flexible drive cable 434 and first proximal drive shaft 414, as a result of the rotation of the first drive shaft of surgical device 310, drive shaft 448 is caused to be translated axially (in the direction of arrow "H") relative to coupling nut 446. Accordingly, as drive shaft 448 is translated axially, with connection member 448c thereof connected to a drive member of any of end effectors 320, 330 and/or 340, drive shaft 448 causes concomitant axial translation of the drive member of any of end effectors 320, 330 and/or 340 to effectuate an operation and/or function thereof. With reference to FIGS. 29 and 30, as drive shaft 452 of second drive converter assembly 450 is rotated (in the direction of arrow "I") due to a rotation of second flexible drive cable 436 and of second proximal drive shaft 416, as a result of the rotation of the second drive shaft of surgical device 310, a drive bar 454 is caused to be translated axially (in the direction of arrow "H") relative to drive shaft 452. Accordingly, as drive bar 454 is translated axially, with hook 454c thereof connected to a drive member of any of end effectors 320, 330 and/or 340, drive bar 454 causes concomitant axial translation of the drive member of any of end effectors 320, 330 and/or 340 to effectuate an operation and/or function thereof. It is envisioned that the cartridge assemblies of the present disclosure may be modified for use with surgical device 310.

It will be understood that various modifications may be made to the embodiment disclosed herein. For example, the presently disclosed circular staplers may include a mechanism for changing cartridge assemblies from two stroke operation to a single stroke operation. Therefore, the above description should not be construed as limiting, but merely as exemplifications of particular embodiments. Those skilled in the art will envision other modifications within the scope and spirit of the claims appended hereto.

The invention claimed is:

1. A method of stapling tissue comprising:
providing a surgical stapling instrument having a pusher and a knife assembly, wherein the knife assembly is selectively fixed relative to the pusher for independent movement relative to the pusher;
advancing the pusher a first distance to cause the ejection and forming of staples;
retracting the pusher a second distance greater than the first distance; and
re-advancing the pusher the second distance to cause the advancement of the knife assembly and the cutting of tissue.

2. The method of claim 1, further including providing a lapse of time between the ejection and forming of the staples and the cutting of tissue to allow for tissue benefit or normalization.

3. The method of claim 1, wherein retracting the pusher includes retracting the pusher to a location proximal of the initial location.

4. The method of claim 1, wherein the knife assembly includes an actuator clip for selectively engaging the pusher.

5. A method of stapling tissue comprising:
advancing a pusher relative to a knife assembly a first distance;
retracting the pusher relative to the knife assembly a second distance greater than the first distance; and
advancing the pusher and the knife assembly the second distance.

6. The method of claim 5, wherein advancing the pusher relative to the knife assembly a first distance effects stapling of tissue.

7. The method of claim 5, wherein retracting the pusher relative to the knife assembly the second distance effects locking of the knife assembly with the pusher.

8. The method of claim 5, wherein advancing the pusher and the knife assembly the second distance effects cutting of tissue.

9. A method of stapling tissue comprising:
advancing a pusher relative to a knife assembly a first distance, wherein advancing the pusher includes squeezing a trigger a first time;
retracting the pusher relative to the knife assembly a second distance greater than the first distance, wherein retracting the pusher includes releasing the trigger following the squeezing of the trigger the first time; and
advancing the pusher and the knife assembly the second distance, wherein advancing the pusher and the knife assembly includes squeezing the trigger a second time following the releasing of the trigger.

10. The method of claim 9, wherein advancing the pusher includes squeezing the trigger the first time at a first rate of speed, and advancing the pusher and the knife assembly includes squeezing the trigger the second time at a second rate of speed.

11. The method of claim 10, wherein squeezing the trigger the first time at the first rate of speed and squeezing the trigger the second time at the second rate of speed varies a staple travel speed relative to a knife travel speed.

12. A method of stapling tissue comprising:
advancing a pusher relative to a knife assembly a first distance;
retracting the pusher relative to the knife assembly a second distance greater than the first distance:
advancing the pusher and the knife assembly the second distance; and
waiting a preselected time between advancing the pusher and advancing the pusher and the knife assembly.

13. A method of stapling tissue comprising:
advancing a pusher relative to a knife assembly a first distance;
retracting the pusher relative to the knife assembly a second distance greater than the first distance;
advancing the pusher and the knife assembly the second distance; and
varying a staple crimp height relative to a knife travel distance by adjusting a distance between a staple cartridge and anvil.

\* \* \* \* \*